United States Patent
Raslambekov

(10) Patent No.: US 11,653,999 B2
(45) Date of Patent: *May 23, 2023

(54) SYSTEMS AND METHODS FOR FORMING A DENTAL APPLIANCE

(71) Applicant: Arkimos Ltd, Larnaca (CY)

(72) Inventor: Islam Khasanovich Raslambekov, Long Island City, NY (US)

(73) Assignee: ARKIMOS Ltd, Larnaca (CY)

( * ) Notice: Subject to any disclaimer, the term of this patent is extended or adjusted under 35 U.S.C. 154(b) by 0 days.

This patent is subject to a terminal disclaimer.

(21) Appl. No.: 17/543,687

(22) Filed: Dec. 6, 2021

(65) Prior Publication Data

US 2022/0211468 A1    Jul. 7, 2022

Related U.S. Application Data

(63) Continuation of application No. 17/143,074, filed on Jan. 6, 2021, now Pat. No. 11,191,618.

(51) Int. Cl.
*G06T 15/00* (2011.01)
*A61C 7/00* (2006.01)
(Continued)

(52) U.S. Cl.
CPC .......... *A61C 7/002* (2013.01); *A61C 13/0004* (2013.01); *A61C 13/0018* (2013.01); *G06T 17/10* (2013.01)

(58) Field of Classification Search
USPC .......................................................... 345/418
See application file for complete search history.

(56) References Cited

U.S. PATENT DOCUMENTS 5,975,893 A    11/1999 Chishti et al.
6,183,248 B1   2/2001 Chishti et al.
(Continued)

FOREIGN PATENT DOCUMENTS

WO    98058596 A1    12/1998
WO    00019928 A1    4/2000
(Continued)

OTHER PUBLICATIONS

Gelaude F, Vander Sloten J, Lauwers B. Accuracy assessment of CT-based outer surface femur meshes. Computer Aided Surgery: Official Journal of the International Society for Computer Aided Surgery. Jul. 1, 2008;13(4):188-99. (Year: 2008).*
(Continued)

*Primary Examiner* — Phu K Nguyen
(74) *Attorney, Agent, or Firm* — BCF LLP

(57) ABSTRACT

A method and a system for manufacturing an orthodontic appliance are provided. The method comprises: receiving a 3D mesh including a plurality of inner vertices representative of an inner surface of the appliance; generating a reference plane positioned relative to the arch form 3D mesh according to a predetermined position; determining, based on the 3D mesh, for each one of the plurality of inner vertices, a respective distance to the reference plane, the respective distance being indicative of a thickness of the appliance after forming; generating, based on the respective distance, a plurality of outer vertices representative of an outer surface of the appliance; generating, based on the plurality of inner vertices and the plurality of outer vertices, an appliance 3D representation of the appliance including data indicative of the thickness of the appliance; causing the manufacturing of the appliance based on the appliance 3D representation.

20 Claims, 10 Drawing Sheets

(51) Int. Cl.
  *A61C 13/00* (2006.01)
  *G06T 17/10* (2006.01)

(56) References Cited

U.S. PATENT DOCUMENTS

| | | | |
|---|---|---|---|
| 6,227,850 B1 | 5/2001 | Chishti et al. |
| 6,309,215 B1 | 10/2001 | Phan et al. |
| 6,318,994 B1 | 11/2001 | Chishti et al. |
| 6,334,853 B1 | 1/2002 | Kopelman et al. |
| 6,386,878 B1 | 5/2002 | Pavlovskaia et al. |
| 6,398,548 B1 | 6/2002 | Muhammad et al. |
| 6,463,344 B1 | 10/2002 | Pavloskaia et al. |
| 6,471,511 B1 | 10/2002 | Chishti et al. |
| 6,554,611 B2 | 4/2003 | Chishti et al. |
| 6,602,070 B2 | 8/2003 | Miller et al. |
| 6,665,570 B2 | 12/2003 | Pavloskaia et al. |
| 6,685,470 B2 | 2/2004 | Chishti et al. |
| 6,688,886 B2 | 2/2004 | Hughes et al. |
| 6,705,863 B2 | 3/2004 | Phan et al. |
| 6,726,478 B1 | 4/2004 | Isiderio et al. |
| 6,739,870 B2 | 5/2004 | Lai et al. |
| 6,767,208 B2 | 7/2004 | Kaza |
| 6,979,196 B2 | 12/2005 | Nikolskiy et al. |
| 7,040,896 B2 | 5/2006 | Pavlovskaia et al. |
| 7,059,850 B1 | 6/2006 | Phan et al. |
| 7,063,532 B1 | 6/2006 | Jones et al. |
| 7,123,767 B2 | 10/2006 | Jones et al. |
| 7,125,248 B2 | 10/2006 | Phan et al. |
| 7,134,874 B2 | 11/2006 | Chishti et al. |
| 7,220,122 B2 | 5/2007 | Chishti |
| 7,241,142 B2 | 7/2007 | Abolfathi et al. |
| 7,293,988 B2 | 11/2007 | Wen |
| 7,320,592 B2 | 1/2008 | Chishti et al. |
| 7,373,286 B2 | 5/2008 | Nikolskiy et al. |
| 7,377,778 B2 | 5/2008 | Chishti et al. |
| 7,428,481 B2 | 9/2008 | Nikolskiy et al. |
| 7,442,040 B2 | 10/2008 | Kuo |
| 7,637,740 B2 | 12/2009 | Knopp |
| 7,689,398 B2 | 3/2010 | Cheng et al. |
| 7,771,195 B2 | 8/2010 | Knopp et al. |
| 7,826,646 B2 | 11/2010 | Pavlovskaia et al. |
| 7,841,858 B2 | 11/2010 | Knopp et al. |
| 7,844,429 B2 | 11/2010 | Matov et al. |
| 7,865,259 B2 | 1/2011 | Kuo et al. |
| 7,904,307 B2 | 3/2011 | Abolfathi et al. |
| 7,905,725 B2 | 3/2011 | Chishti et al. |
| 7,942,672 B2 | 5/2011 | Kuo |
| 7,993,134 B2 | 8/2011 | Wen |
| 8,026,916 B2 | 9/2011 | Wen |
| 8,038,444 B2 | 10/2011 | Kitching et al. |
| 8,044,954 B2 | 10/2011 | Kitching et al. |
| 8,105,080 B2 | 1/2012 | Chishti et al. |
| 8,108,189 B2 | 1/2012 | Chelnokov et al. |
| 8,131,393 B2 | 3/2012 | Matov et al. |
| 8,135,569 B2 | 3/2012 | Matov et al. |
| 8,244,390 B2 | 8/2012 | Kuo et al. |
| 8,439,672 B2 | 5/2013 | Matov et al. |
| 8,465,280 B2 | 6/2013 | Sachdeva et al. |
| 8,478,435 B2 | 7/2013 | Kuo et al. |
| 8,509,933 B2 | 8/2013 | Steingart et al. |
| 8,639,477 B2 | 1/2014 | Chelnokov et al. |
| 8,641,414 B2 | 2/2014 | Borovinskih et al. |
| 8,734,150 B2 | 5/2014 | Wen |
| 8,780,106 B2 | 7/2014 | Chishti et al. |
| 8,807,999 B2 | 8/2014 | Kuo et al. |
| 8,896,592 B2 | 11/2014 | Boltunov et al. |
| 8,897,902 B2 | 11/2014 | See et al. |
| 8,961,173 B2 | 2/2015 | Miller |
| 9,060,829 B2 | 6/2015 | Sterental et al. |
| 9,107,722 B2 | 8/2015 | Matov et al. |
| 9,161,823 B2 | 10/2015 | Morton et al. |
| 9,161,824 B2 | 10/2015 | Chishti et al. |
| 9,211,166 B2 | 12/2015 | Kuo et al. |
| 9,326,831 B2 | 5/2016 | Cheang |
| 9,345,557 B2 | 5/2016 | Anderson et al. |
| 9,375,293 B2 | 6/2016 | Taub et al. |
| 9,375,300 B2 | 6/2016 | Matov et al. |
| 9,414,897 B2 | 8/2016 | Wu et al. |
| 9,433,476 B2 | 9/2016 | Khardekar et al. |
| 9,529,970 B2 | 12/2016 | Andreiko |
| 9,592,103 B2 | 3/2017 | Taub et al. |
| 9,610,140 B2 | 4/2017 | Anderson et al. |
| 9,622,834 B2 | 4/2017 | Chapoulaud et al. |
| 9,792,413 B2 | 10/2017 | Badawi |
| 9,844,424 B2 | 12/2017 | Wu et al. |
| 10,011,050 B2 | 7/2018 | Kitching et al. |
| 10,076,389 B2 | 9/2018 | Wu et al. |
| 10,307,222 B2 | 6/2019 | Morton et al. |
| 10,332,164 B2 | 6/2019 | Abolfathi et al. |
| 10,350,030 B2 | 7/2019 | Rubbert et al. |
| 10,357,336 B2 | 7/2019 | Wen |
| 10,383,704 B2 | 8/2019 | Kitching |
| 10,390,913 B2 | 8/2019 | Sabina et al. |
| 10,405,947 B1 | 9/2019 | Kaza et al. |
| 10,405,951 B1 | 9/2019 | Kopelman et al. |
| 10,413,385 B2 | 9/2019 | Sherwood et al. |
| 10,433,934 B2 | 10/2019 | Kopelman |
| 10,463,452 B2 | 11/2019 | Matov et al. |
| 10,470,846 B2 | 11/2019 | Kopelman et al. |
| 10,517,482 B2 | 12/2019 | Sato et al. |
| 10,524,880 B2 | 1/2020 | Wen |
| 10,548,690 B2 | 2/2020 | Wen |
| 10,553,309 B2 | 2/2020 | Trosien et al. |
| 10,561,476 B2 | 2/2020 | Matov et al. |
| 10,595,965 B2 | 3/2020 | Khardekar et al. |
| 10,617,489 B2 | 4/2020 | Grove et al. |
| 10,631,953 B2 | 4/2020 | Wen |
| 10,650,517 B2 | 5/2020 | Parpara et al. |
| 10,653,503 B2 | 5/2020 | Boltunov et al. |
| 10,783,629 B2 | 9/2020 | Parpara et al. |
| 10,792,127 B2 | 10/2020 | Kopelman et al. |
| 10,803,675 B2 | 10/2020 | Lancelle et al. |
| 10,813,721 B2 | 10/2020 | Sterental et al. |
| 10,881,486 B2 | 1/2021 | Wen |
| 11,191,618 B1* | 12/2021 | Raslambekov ........ A61C 7/002 |
| 2005/0244791 A1 | 11/2005 | Davis et al. |
| 2013/0095446 A1 | 4/2013 | Andreiko et al. |
| 2014/0288894 A1 | 9/2014 | Chishti et al. |
| 2016/0302885 A1 | 10/2016 | Matov et al. |
| 2017/0035536 A1 | 2/2017 | Alvarez Garcia et al. |
| 2017/0079748 A1 | 3/2017 | Andreiko |
| 2017/0136576 A1* | 5/2017 | Ashihara ................. B08B 5/02 |
| 2018/0039755 A1 | 2/2018 | Matov et al. |
| 2018/0165818 A1 | 6/2018 | Tsai et al. |
| 2018/0303581 A1 | 10/2018 | Martz et al. |
| 2018/0304497 A1 | 10/2018 | Kitching et al. |
| 2019/0000592 A1 | 1/2019 | Cam et al. |
| 2019/0046295 A1 | 2/2019 | Morton et al. |
| 2019/0175303 A1 | 6/2019 | Akopov et al. |
| 2019/0282333 A1 | 9/2019 | Matov et al. |
| 2019/0314117 A1 | 10/2019 | Morton et al. |
| 2019/0357997 A1 | 11/2019 | Shi et al. |
| 2020/0000551 A1 | 1/2020 | Li et al. |
| 2020/0000552 A1 | 1/2020 | Mednikov et al. |
| 2020/0018082 A1* | 1/2020 | Claro Carrascal ...... E04G 11/40 |
| 2020/0146776 A1 | 5/2020 | Matov et al. |
| 2020/0229900 A1 | 7/2020 | Cunliffe et al. |
| 2020/0297459 A1 | 9/2020 | Grove et al. |
| 2020/0306011 A1 | 10/2020 | Chekhonin et al. |
| 2020/0306012 A1 | 10/2020 | Roschin et al. |
| 2020/0311934 A1 | 10/2020 | Cherkas et al. |
| 2020/0320685 A1 | 10/2020 | Anssari et al. |

FOREIGN PATENT DOCUMENTS

| | | | |
|---|---|---|---|
| WO | 00019930 A1 | 4/2000 |
| WO | 00019931 A1 | 4/2000 |
| WO | 00069356 A1 | 11/2000 |
| WO | 00069357 A1 | 11/2000 |
| WO | 01074268 A1 | 11/2001 |
| WO | 2018085718 A2 | 5/2018 |
| WO | 2019089989 A2 | 5/2019 |
| WO | 2019217764 A1 | 11/2019 |
| WO | 2020182880 A1 | 9/2020 |

(56) References Cited

FOREIGN PATENT DOCUMENTS

OTHER PUBLICATIONS

Zhang ey al. "An Effective Approach of Teeth Segmentation within the 3D Cone Beam Computed Tomography Image Based on Deformable Surface Model", Mathematical Problems in Engineering, vol. 2016, Article ID 9505217, 10 pages, 2016. https://doi.org/10.1155/2016/9505217.

Barone et al., "Computational design and engineering of polymeric orthodontic aligners", Published on Oct. 5, 2016, International Journal for Numerical Methods in Biomedical Engineering, vol. 33, Issue 8, https://doi.org/10.1002/cnm.2839.

Gonzalez et al., "Polymers for additive manufacturing and 4D-printing: Materials, methodologies, and biomedical applications", Published on Jul. 2019, vol. 94, pp. 57-116, http://doi.org/10.1016/j.progpolymsci.2019.03.001.

* cited by examiner

SYSTEMS AND METHODS FOR FORMING A DENTAL APPLIANCE

CROSS-REFERENCE

The present application is a Continuation of U.S. patent application Ser. No. 17/143,074, filed on Jan. 6, 2021, content of which is incorporated herein by reference in its entirety.

FIELD

The present technology relates to systems and methods for manufacturing a dental appliance; and more specifically, although not exclusively, to manufacturing the dental appliance based on thickness distribution thereof.

BACKGROUND

In orthodontics, treatments for achieving alignment of malposed teeth in a subject include applying dental appliances, such as orthodontic aligners, to subject's teeth. Orthodontic aligners are typically worn over teeth of an arch form in order to exert a force to the subject's teeth to move the teeth to a desired position, such as to align malocclusions. Generally, physical parameters of the aligner, such as its internal shape, type of material, and thickness, among other factors, define the respective forces exerted to the subject's teeth and the effective correction that may be attained. An orthodontic treatment plan for moving the teeth to the desired position may comprise multiple sequential treatment steps in which different aligners, each with a different physical parameters are to be worn by the subject.

Orthodontic aligners are typically custom-made to the subject's teeth and based on 3D representations of the subject's teeth.

Aligners can be made by a thermoforming process, in which a preform is shaped using a mold to produce an unfinished aligner. The unfinished aligner is further processed, such as by trimming excess material along a cut line to produce an edge of the aligner. Such an edge may be designed to correspond to a gum-tooth boundary of the subject for comfort. The trimming may be executed by using a cutting tool, such as a laser cutting tool or a mechanical cutting tool.

However, thermoforming methods are susceptible to produce variations in the unfinished aligner thickness. Thermoforming parameters such as applied heat and pressure, as well as preform thickness may affect the thickness of the aligner. Such variations in the unfinished aligner can create problems during cutting, leading to undesired configurations along the cut line which can be a source of discomfort to the subject or may result in a deviation from the planned orthodontic treatment. For example, the cutting tool may more easily cut through thinner portions of the unfinished aligner compared to thicker portions, resulting in the thicker portions having a more ragged finish.

Certain approaches addressing the above-identified technical problem have been proposed in the prior art.

United States Patent Application Publication No.: 2020/0311934-A1 published on Oct. 1, 2020, assigned to Align Technology Inc., and entitled "Vision and Geometric Approaches to Detect Defects in Dental Appliances" discloses multiple techniques for detecting defects in customized dental appliances. In one technique, processing logic obtains one or more images of a customized dental appliance, obtains a digital model associated with the customized dental appliance, and performs segmentation on the one or more images to identify an area of the one or more images that comprises a representation of the customized dental appliance. Processing logic then registers the one or more images to the digital model, compares the area of the one or more images of the customized dental appliance with the digital model of the customized dental appliance, determines a difference between the area of the one or more images that comprises the representation of the customized dental appliance and the digital model of the customized dental appliance at a region, and determines whether the difference satisfies a defect criterion.

U.S. Pat. No. 10,517,482-B2 issued on Dec. 31, 2019, assigned to Align Technology Inc., and entitled "Optical Coherence Tomography for Orthodontic Aligners" discloses methods and apparatuses for 3D imaging (including 3D optical coherence tomography imaging) to measure the shape of orthodontic aligners, teeth, and other oral structures simultaneously, in-vivo or in-vitro. These methods and apparatuses may be used to determine contact locations of aligners with teeth and/or teeth with other teeth with very high precision, including determining the size of gaps where they are not in contact. These measurements may be used design, modify or replace an aligner and/or to verify aligner fit. 3D models of the whole aligner and teeth may be generated.

U.S. Patent Application Publication No.: US 2020/0306011-A1 published on Oct. 1, 2020, assigned to Align Technology Inc., and entitled "Prediction of Multiple Treatment Settings" discloses orthodontic and/or dental treatment planning methods and apparatuses. In particular, the described methods are directed to generating a plurality of potential treatment plan variations for the concurrent and interactive review of the treatment plan variations. Also described are orthodontic and/or dental treatment planning methods and apparatuses that present the plurality of treatment plans to the user to allow a user to select a treatment plan from a plurality of different treatment plans.

U.S. Patent Application Publication No.: 2018/0303581-A1 published on Oct. 25, 2018, assigned to Archform Inc., and entitled "Fabrication of Dental Appliances" discloses systems and method for fabrication of dental appliances. An example method includes receiving data identifying approximate locations of individual teeth in a three-dimensional digital dental model representing an impressioned position of a patient's dentition. The example method may also include generating component models corresponding to individual teeth for each of the identified approximate locations. The component models may be disposed at initial positions based on the impressioned position of the patient's dentition. The example method also includes determining target positions for the component models and generating a tooth-positioning appliance design based on the determined target positions for the component models. The method may also include causing a tooth-positioning appliance to be fabricated based on the tooth-positioning appliance design.

SUMMARY

It is an object of the present technology to ameliorate at least some of the inconveniences present in the prior art.

Developers of the present technology have realized that there would be advantages associated with modelling more closely the obtained unfinished aligner, including its thickness variation, before the cutting step. For example, the cutting could be made more efficient if an aligner thickness distribution could be preliminarily assessed. Further, the developers have appreciated that at least one parameter associated with the cutting tool may be adjusted during the cutting the unfinished aligner based on variations of thickness along the cut line in order to obtain a desired finish along the edge of the aligner.

More specifically, non-limiting embodiments of the present technology are directed to methods and the systems for generating an aligner 3D representation of the aligner by: receiving an aligner mold 3D representation of the arch form mold associated with a given stage of the orthodontic treatment, the aligner mold 3D representation defining an inner surface of the aligner; constructing a cover surface encompassing the plurality of inner vertices; determining a respective distance from each of the vertices of the arch form 3D representation to the cover surface, wherein the respective distance is indicative of the aligner thickness distribution within the aligner; determining an outer surface of the aligner based on the respective distance; and generating, based on the inner surface and the outer surface, the aligner 3D representation including the thickness variation.

Further, certain non-limiting embodiments of the methods and systems described herein are directed to receiving data indicative of a predetermined cut line for the aligner and determining a thickness of the aligner along the cut line. Accordingly, the thickness of the aligner along the cut line may be used for adjusting the parameters of the cutting tool to obtain a more optimized cutting, either in terms of the obtained edge of the aligner or an efficiency of the cutting. Optimization of cutting may include an intensity of the cutting tool or a distance of the cutting tool from the unfinished aligner during cutting. As a result, the present methods and systems may allow cutting the unfinished aligner in a more energy-efficient fashion, which may further provide a higher quality of cutting associated, for example, with a smoother open edge of the aligner.

More specifically, in accordance with a first broad aspect of the present technology, there is provided a method of manufacturing an orthodontic appliance for a subject. The method is executable by a processor. The method comprises: receiving, by the processor, a 3D mesh including an arch form 3D representation of an arch form mold associated with the subject used for manufacturing the orthodontic appliance, the 3D mesh including a plurality of inner vertices representative of an inner surface of the orthodontic appliance; generating, by the processor, a reference plane positioned relative to the arch form 3D representation according to a predetermined position and such that the reference plane is spaced from at least some of the plurality of inner vertices; determining, by the processor, based on the 3D mesh, for each one of the plurality of inner vertices, over a respective normal vector to the inner surface of the orthodontic appliance, a respective distance to the reference plane, the respective distance associated with a given inner vertex being indicative of a thickness of the orthodontic appliance after forming a preform on the arch form mold; determining, by the processor, based on the respective distance, for each one of the plurality of inner vertices, a respective offset distance for displacement thereof along the respective normal vector, thereby generating a plurality of outer vertices representative of an outer surface of the orthodontic appliance; generating, by the processor, based on the plurality of inner vertices and the plurality of outer vertices, an orthodontic appliance 3D representation of the orthodontic appliance including data indicative of a thickness of the orthodontic appliance after forming the preform on the arch form mold; causing the manufacturing of the orthodontic appliance based at least in part on the orthodontic appliance 3D representation.

From another broad aspect of the present technology, there is provided a method of modelling an orthodontic appliance for a subject. The method is executable by a processor. The method comprises: receiving, by the processor, a 3D mesh including an arch form 3D representation of an arch form mold associated with the orthodontic appliance, the 3D mesh including a plurality of inner vertices representative of an inner surface of the orthodontic appliance; generating, by the processor, a reference plane positioned relative to the arch form 3D representation according to a predetermined position and such that the reference plane is spaced from at least some of the plurality of inner vertices; determining, by the processor, based on the 3D mesh, for each one of the plurality of inner vertices, over a respective normal vector to the inner surface of the orthodontic appliance, a respective distance to the reference plane, the respective distance associated with a given inner vertex being indicative of a thickness of the orthodontic appliance after forming a preform on the arch form mold; determining, by the processor, based on the respective distance, for each one of the plurality of inner vertices, a respective offset distance for displacement thereof along the respective normal vector, thereby generating a plurality of outer vertices representative of an outer surface of the orthodontic appliance; generating, by the processor, based on the plurality of inner vertices and the plurality of outer vertices, an orthodontic appliance 3D representation of the orthodontic appliance including data indicative of a thickness of the orthodontic appliance after forming the preform on the arch form mold.

In some implementations of the method, the 3D mesh further includes, along with the arch form 3D representation: a support surface 3D representation indicative of a support surface used for forming the orthodontic appliance from the preform, the arch form 3D representation being positioned on the support surface 3D representation; and wherein the determining the respective distance from each one of the plurality of inner vertices further comprises: generating a cover surface encompassing the plurality of inner vertices of the 3D mesh, the cover surface including the reference plane and at least a portion of the support surface 3D representation; and determining the respective distance to the cover surface.

In some implementations of the method, the method further comprises converting the 3D mesh into a voxel space and obtaining the plurality of inner vertices therefrom, the plurality of inner vertices having been redistributed within the 3D mesh uniformly.

In some implementations of the method, the manufacturing comprises the processor causing the forming of the preform to manufacture the orthodontic appliance based on the orthodontic appliance 3D representation.

In some implementations of the method, the method further comprises obtaining data indicative of a cut line for the orthodontic appliance, and wherein the manufacturing comprising causing, by the processor, cutting, by a cutting device, the orthodontic appliance along the cut line.

In some implementations of the method, the method further comprises determining, by the processor, the cut line for the orthodontic appliance based at least on the 3D mesh.

In some implementations of the method, the method further comprises determining, based on the orthodontic appliance 3D representation, a thickness of the orthodontic appliance along the cut line; and the manufacturing comprising, based on the thickness of the orthodontic appliance along the cut line, causing, by the processor, a cutting device to cut the orthodontic appliance along the cut line.

In some implementations of the method, the cutting device includes a laser apparatus, and wherein the causing comprises modulating, by the processor, a parameter of the laser apparatus based on the thickness of the orthodontic appliance 3D representation along the cut line.

In some implementations of the method, the method further comprises: visualizing, on the orthodontic appliance 3D representation, the respective distances associated with the inner plurality of vertices, thereby generating a heat map representative of a thickness distribution within the orthodontic appliance. The method may include storing the orthodontic appliance 3D representation including the heat map. The method may include causing display of the orthodontic appliance 3D representation including the heat map on a display.

In some implementations of the method, a given offset distance associated with a respective one of the plurality of inner vertices is determined based on the following equation:

$$\|n\| = h - kp$$

where $\|n\|$ is the given offset distance;
h is an initial thickness of the preform;
k is a predetermined coefficient; and
p is a respective distance from the respective one of the plurality of inner vertices to the reference plane having been determined along a respective normal vector.

In some implementations of the method, the predetermined coefficient is determined such that the following equation is satisfied:

$$V_o = V_f$$

where $V_o$ is a volume of the preform; and
$V_f$ is a volume of the orthodontic appliance.

In accordance with a second broad aspect of the present technology, there is provided a system for manufacturing an orthodontic appliance. The system comprises: a processor and a non-transitory computer-readable medium comprising instructions. The processor, upon executing the instructions, is configured to: receive a 3D mesh including at least an arch form 3D representation of an arch form mold associated with the subject used for manufacturing the orthodontic appliance, the 3D mesh including a plurality of inner vertices representative of an inner surface of the orthodontic appliance, the 3D mesh; generate a reference plane positioned relative to the arch form 3D representation according to a predetermined position and such that the reference plane is spaced from at least some of the plurality of inner vertices; determine, based on the 3D mesh, for each one of the plurality of inner vertices, over a respective normal vector to the inner surface of the orthodontic appliance, a respective distance to the reference plane, the respective distance associated with a given inner vertex being indicative of a thickness of the orthodontic appliance after forming a preform on the arch form mold; determine, based on the respective distance, for each one of the plurality of inner vertices, a respective offset distance for displacement thereof along the respective normal vector, thereby generating a plurality of outer vertices representative of an outer surface of the orthodontic appliance; generate, based on the plurality of inner vertices and the plurality of outer vertices, an orthodontic appliance 3D representation of the orthodontic appliance including data indicative of a thickness of the orthodontic appliance after forming the preform on the arch form mold; cause manufacturing of the orthodontic appliance based at least in part on the orthodontic appliance 3D representation.

In accordance with another broad aspect of the present technology, there is provided a system for modelling an orthodontic appliance. The system comprises: a processor and a non-transitory computer-readable medium comprising instructions. The processor, upon executing the instructions, is configured to: receive a 3D mesh including at least an arch form 3D representation of an arch form mold associated with the subject used for manufacturing the orthodontic appliance, the 3D mesh including a plurality of inner vertices representative of an inner surface of the orthodontic appliance, the 3D mesh; generate a reference plane positioned relative to the arch form 3D representation according to a predetermined position and such that the reference plane is spaced from at least some of the plurality of inner vertices; determine, based on the 3D mesh, for each one of the plurality of inner vertices, over a respective normal vector to the inner surface of the orthodontic appliance, a respective distance to the reference plane, the respective distance associated with a given inner vertex being indicative of a thickness of the orthodontic appliance after forming a preform on the arch form mold; determine, based on the respective distance, for each one of the plurality of inner vertices, a respective offset distance for displacement thereof along the respective normal vector, thereby generating a plurality of outer vertices representative of an outer surface of the orthodontic appliance; generate, based on the plurality of inner vertices and the plurality of outer vertices, an orthodontic appliance 3D representation of the orthodontic appliance including data indicative of a thickness of the orthodontic appliance after forming the preform on the arch form mold.

In some implementations of the system, the 3D mesh further includes, along with the arch form 3D representation: a support surface 3D representation indicative of a support surface used for forming the orthodontic appliance from the preform, the arch form 3D representation being positioned on the support surface 3D representation; and wherein to determine the respective distance from each one of the plurality of inner vertices further comprises, the processor is further configured to: generate a cover surface encompassing the plurality of inner vertices of the 3D mesh, the cover surface including the reference plane and at least a portion of the support surface 3D representation; and determine the respective distance to the cover surface.

In some implementations of the system, the processor is further configured to convert the 3D mesh into a voxel space and obtaining the plurality of inner vertices therefrom, the plurality of inner vertices having been redistributed within the 3D mesh uniformly.

In some implementations of the system, to cause the manufacturing the orthodontic appliance based on the orthodontic appliance 3D representation, the processor is further configured to cause the forming of the preform.

In some implementations of the system, the system further comprises a cutting device communicatively coupled with the processor, and wherein the processor is further configured to: obtain data indicative of a cut line for the orthodontic appliance; cause the cutting device to cut the orthodontic appliance along the cut line.

In some implementations of the system, the processor is configured to determine the cut line for the orthodontic appliance based at least on the 3D mesh.

In some implementations of the system, the processor is further configured to determine, based on the orthodontic appliance 3D representation, a thickness of the orthodontic appliance along the cut line; and the manufacturing comprising, based on the thickness of the orthodontic appliance along the cut line, causing, by the processor, a cutting device to cut the orthodontic appliance along the cut line.

In some implementations of the system, the cutting device includes a laser apparatus, and wherein the processor is configured to cause the laser apparatus to modulate a parameter thereof based on the thickness of the orthodontic appliance 3D representation along the cut line.

In some implementations of the system, the cutting device includes a laser apparatus, and wherein the processor is configured to cause the laser apparatus to modulate a parameter thereof based on a thickness of the orthodontic appliance 3D representation along the cut line.

In some implementations of the system, the processor is further configured to: visualize, on the orthodontic appliance 3D representation, the respective distances associated with the inner plurality of vertices, thereby generating a heat map representative of a thickness distribution within the orthodontic appliance; store the orthodontic appliance 3D representation including the heat map; and cause display of the orthodontic appliance 3D representation including the heat map on a display.

In some implementations of the system, the processor is configured to determine a given offset distance associated with a respective one of the plurality of inner vertices based on the following equation:

$$\|n\|=h-kp$$

where $\|n\|$ is the given offset distance;
h is an initial thickness of the preform;
k is a predetermined coefficient; and
p is a respective distance from the respective one of the plurality of inner vertices to the reference plane having been determined along a respective normal vector.

In some implementations of the system, the predetermined coefficient is determined such that the following equation is satisfied:

$$V_0 = V_f$$

where $V_0$ is a volume of the preform; and
$V_f$ is a volume of the orthodontic appliance.

In the context of the present specification, the term "orthodontic treatment" is broadly referred to as any type of medical intervention aimed at correcting malocclusions associated with the subject's teeth, including surgical and non-surgical manipulations, such as, but not limited to, using aligners. Further, the orthodontic treatment, as referred to herein, may be determined by a professional practitioner in the field of dentistry (such as an orthodontist, a maxillofacial surgeon, for example), or automatically by a specific software, based on respective image data and input parameters associated with the subject.

Further, in the context of the present specification, the term "cut line" refers to a contour extending around a given unfinished aligner (such as that produced through thermoforming of a respective preform on a mold) for defining an edge of an open end (channel) of an aligner for the subject.

In the context of the present specification, unless expressly provided otherwise, a computer system may refer, but is not limited to, an "electronic device", an "operation system", a "system", a "computer-based system", a "controller unit", a "control device" and/or any combination thereof appropriate to the relevant task at hand.

In the context of the present specification, unless expressly provided otherwise, the expression "computer-readable medium" and "memory" are intended to include media of any nature and kind whatsoever, non-limiting examples of which include RAM, ROM, disks (CD-ROMs, DVDs, floppy disks, hard disk drives, etc.), USB keys, flash memory cards, solid state-drives, and tape drives.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, unless expressly provided otherwise, the words "first", "second", "third", etc. have been used as adjectives only for the purpose of allowing for distinction between the nouns that they modify from one another, and not for the purpose of describing any particular relationship between those nouns.

Embodiments of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of embodiments of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

It should be noted that, unless otherwise explicitly specified herein, the drawings are not to scale.

DETAILED DESCRIPTION

Certain aspects and embodiments of the present technology are directed to methods of and systems for manufacturing an orthodontic appliance.

More specifically, certain aspects and embodiments of the present technology comprise a computer-implemented method of manufacturing the orthodontic appliance including determining a thickness distribution within the orthodontic appliance; generating, based on the thickness distribution, an appliance 3D representation of the orthodontic appliance; and based on the appliance 3D representation, forming the orthodontic appliance. In some non-limiting embodiments of the present technology, the forming may comprise cutting an unfinished orthodontic appliance, produced, for example, via a thermoforming process, along a predetermined cut line modulating at least one parameter of an associated cutting device based on the thickness distribution within the orthodontic appliance along the cut line.

Certain embodiments of the present technology minimize, reduce or avoid some of the problems noted with the prior art. For example, by implementing certain embodiments of the current technology in respect of determining the cut line, one or more of the following advantages may be obtained: (1) a more efficient power consumption associated with the cutting tool configured to cut along the cut line for forming the orthodontic appliance—such as electrical power used for powering a laser cutting tool, for example; (2) a smoother open edge of the finished orthodontic appliance defined by the cut line; and (3) a thus produced open edge which corresponds more closely to a desired open edge for a desired comfort and/or orthodontic treatment effect. Thus, methods and systems provided herein, according to certain non-limiting embodiments of the present technology, allow reducing power consumption for producing the orthodontic appliance and/or provide for higher quality of the resulting cut of the open edge of the orthodontic appliance.

Orthodontic Treatment

Figure 1:
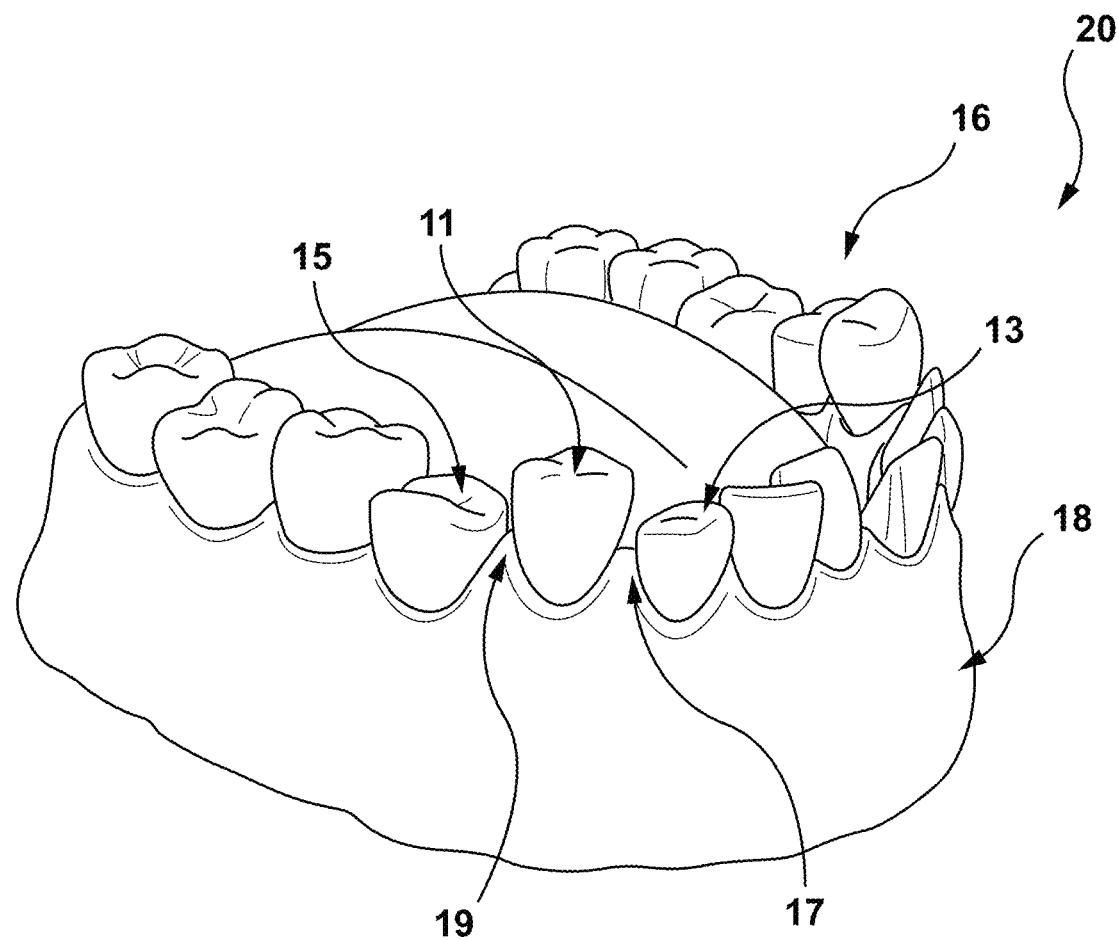
FIG. 1 depicts a perspective view of a lower arch form of a subject depicting examples of malocclusions of some of subject's teeth, in accordance with certain non-limiting embodiments of the present technology.

Referring initially to FIG. 1, there is depicted a perspective view of a lower arch form 20 of the subject, to which certain aspects and non-limiting embodiments of the present technology may be applied.

As can be appreciated, the lower arch form 20 includes lower teeth 16 and a lower gingiva 18. Further, in the depicted embodiments of FIG. 1, positions of at least some of the lower teeth 16 within the lower arch form 20 may be indicative of certain orthodontic disorders of the subject. For example, at least a first tooth 11, a second tooth 13, and a third tooth 15 are misaligned within the lower arch form 20. Further, some of the lower teeth 16 may form excessive interdental spaces, such as a first interdental space 17 formed between the first tooth 11 and the second tooth 13; and a second interdental space 19 formed between the first tooth 11 and the third tooth 15.

Other examples of the orthodontic disorders (not depicted) associated with malpositions of lower teeth relative to each other and to an upper arch form (not depicted), according to certain non-limiting embodiments of the present technology, may include, without limitation: overbites, underbites, crossbites, openbites, crowding of some of the lower teeth 16, and others.

In some non-limiting embodiments of the present technology, for resolving the above-mentioned orthodontic disorders, an orthodontic treatment may be provided to the subject.

In some non-limiting embodiments of the present technology, the orthodontic appliances may comprise applying an orthodontic appliance. Generally speaking, the orthodontic appliance may be configured to exert a respective predetermined force onto at least one of the first tooth 11, the second tooth 13, and the third tooth 15 causing them to move towards an aligned position, that is, the position associated with normal occlusion between the lower teeth 16 and upper teeth (not depicted) of the subject. More specifically, in the depicted embodiments of FIG. 1, the orthodontic appliance may be configured to cause the first tooth 11 to move outwardly between the second tooth 13 and the third tooth 15; and further cause intrusion thereof in tissues of the lower gingiva 18. Further, the orthodontic appliance may be configured to cause the second tooth 13 to rotate clockwise around its tooth axis, and to cause the third tooth 15 to move inwardly relative to the lower arch form 20. In various non-limiting embodiments of the present technology, the orthodontic appliance may comprise orthodontic appliances of different types, shapes, sizes and configurations, such as those including, without limitation, aligners, brackets, multistrand wires, strips, retainers, and plates.

In some non-limiting embodiments of the present technology, the orthodontic appliance may be selected, in the course of the orthodontic treatment, based on a respective orthodontic disorder. For example, in some non-limiting embodiments of the present technology, the orthodontic appliance may include a biteplate (not depicted) used for correcting the overbites. More specifically, the biteplate may be configured for preventing front ones of upper teeth (not depicted) of the upper arch form (not depicted) overlap front ones of the lower teeth 16 for extended periods of time.

Further, in some non-limiting embodiments of the present technology, the orthodontic appliance may include a bitesplint (not depicted), which may be applied to the lower teeth 16 for correcting the crossbites—a lateral misalignment of one of the lower arch form 20 and the upper arch form (not depicted) resulting, for example, in buccal surfaces of some of the upper teeth (not depicted) overlapping lingual surfaces of corresponding ones of the lower teeth 16. To that end, the bitesplint may be configured for preventing the subject from biting completely, which may further allow correcting the crossbites.

Figure 2A:
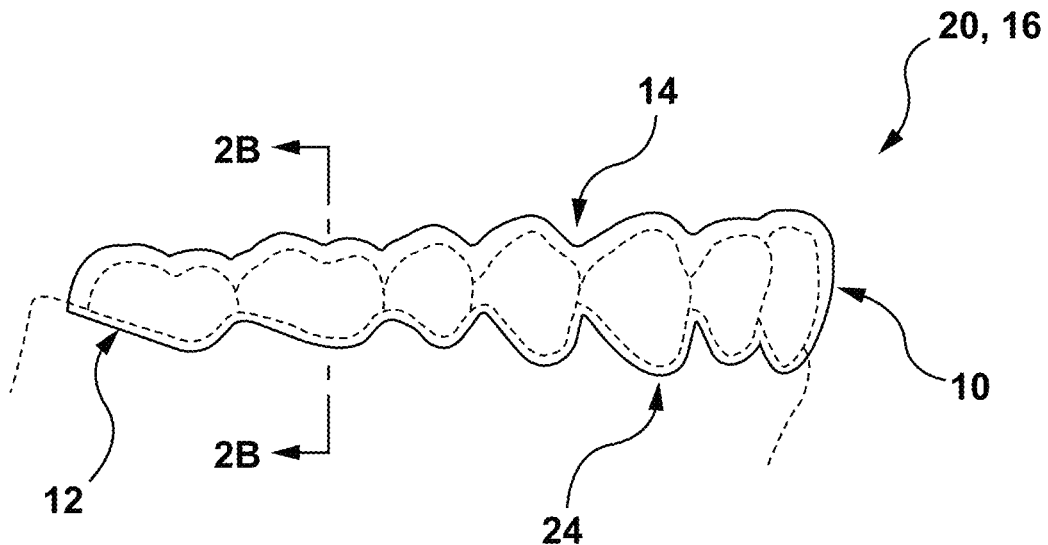
FIGS. 2A and 2B depict side and cross-sectional views, respectively, of a dental appliance applied to the subject's teeth that may be configured to treat the malocclusions of the subject's teeth present in FIG. 1, in accordance with certain non-limiting embodiments of the present technology.
Figure 2B:
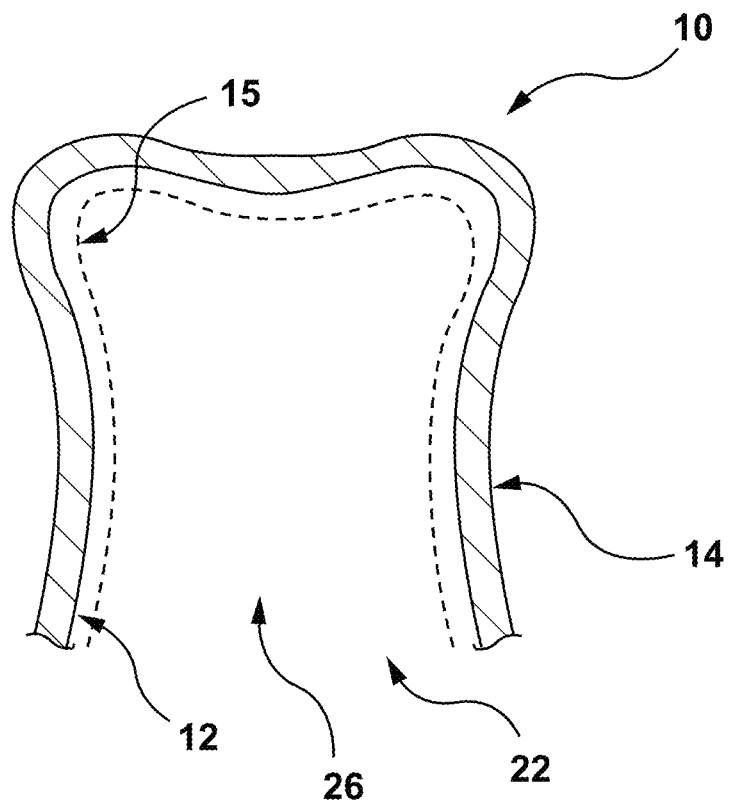

In specific non-limiting embodiments of the present the present technology, the orthodontic appliance may include an aligner. With reference to FIGS. 2A and 2B, there is depicted an aligner 10 applied to at least some of the lower teeth 16, in accordance with certain non-limiting embodiments of the present technology. The aligner 10 comprises an inner surface 12 and an outer surface 14. The inner surface 12 defines a channel 26, which is configured, in some non-limiting embodiments of the present technology, for receiving crown portions of at least some of the lower teeth 16 including the first tooth 11, the second tooth 13, and the third tooth 15. However, in other non-limiting embodiments of the present technology, the channel 26 of the aligner 10 may be configured to receive crown portions of all of the lower teeth 16. At least one edge (also referred to herein as an "open edge", defined by a cut line 304 depicted in FIG. 3, for example) of the channel 26 is shaped for following a gum line 22 along the lower gingiva 18.

It is appreciated that, in accordance with certain non-limiting embodiments of the present technology, the aligner 10 may be used for treating different types of teeth misalignment or malocclusion, including but not limited to one or more of: closing interdental spaces ("space closure"), creating/widening interdental spaces, tooth rotation, tooth intrusion/extrusion, and tooth translation, to name a few. It should further be noted that in certain non-limiting embodiments of the present technology, applying the aligner 10 to the lower teeth 16 may further include applying specific attachments thereto.

As may become apparent, the aligner 10 may be designed in such a way that its inner surface 12 is configured to impose respective forces on one or more of the lower teeth 16 to obtain a desired position of the lower teeth 16 at a given stage of the orthodontic treatment.

Needles to say that, although in the depicted embodiments of FIGS. 2A and 2B, the aligner 10 is configured to be applied onto the lower teeth 16, in other non-limiting embodiments of the present technology, a respective configuration of the aligner 10 may be applied to the upper teeth (not depicted) of the subject for conducting the orthodontic treatment of respective malocclusion disorders.

According to certain non-limiting embodiments of the present technology, the aligner 10 may be made of a polymer, such as a thermoplastic material. In other non-limiting embodiments of the present technology, the aligner 10 may be made of poly-vinyl chloride (PVC). In yet other non-limiting embodiments of the present technology, the aligner 10 may be made of polyethylene terephthalate glycol (PETG). Other suitable materials can also be used to form the aligner 10.

In some non-limiting embodiments of the present technology, the aligner 10 may be manufactured using additive manufacturing techniques, such as 3D printing techniques where the aligner 10 is formed by printing according to a pre-generated 3D representation thereof.

However, in other non-limiting embodiments of the present technology, the aligner 10 may be produced by a thermoforming process where (1) an unfinished aligner is produced, using a preform, on a respective aligner mold (not depicted) associated with a respective stage of the orthodontic treatment, which is configured to shape the inner surface 12 of the aligner 10; and (2) the unfinished aligner is cut along the cut line 304 to remove excess material therefrom, thereby producing the aligner 10, the cut line 304 defining the at least one edge of the channel 26 of the aligner 10.

As an artefact of the thermoforming process, the aligner 10 may have a variable thickness throughout. This may affect a magnitude of a given force applied, via the aligner 10, to a given one of the lower teeth 16. For example, as depicted in FIG. 2B, considering the third tooth 15, if portions of the aligner 10 associated with an occlusal surface of the third tooth 15 have greater thickness than those corresponding to side surfaces thereof, a greater force may be applied by those portions of the aligner 10.

Figure 3:
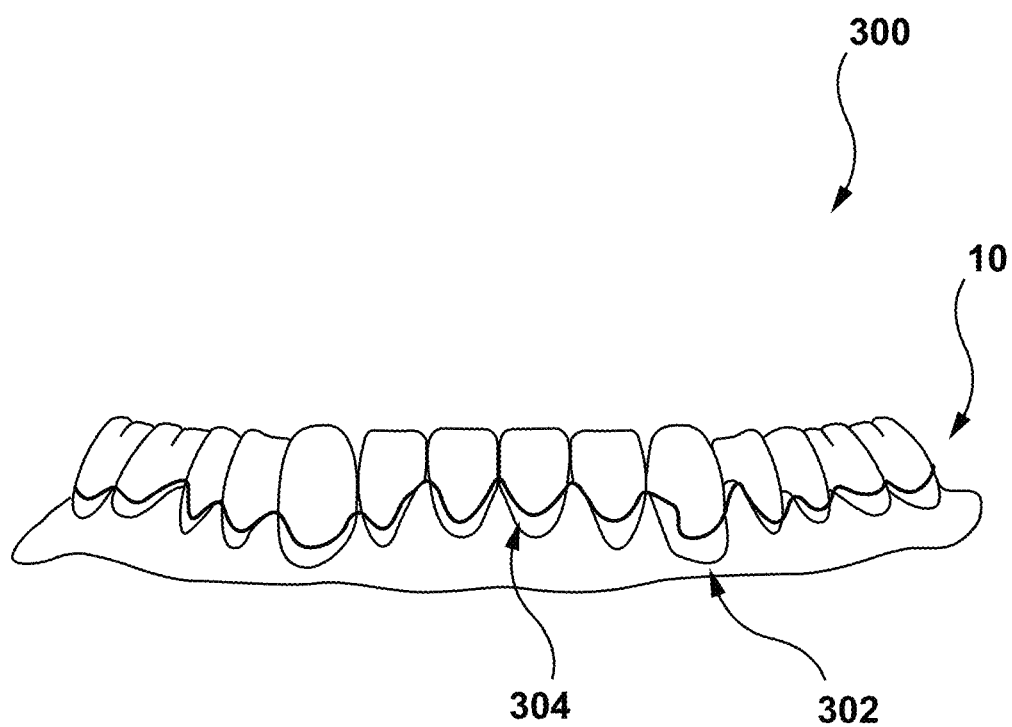
FIG. 3 depicts a panoramic view of an unfinished dental appliance with a cut line applied thereon used for manufacturing the dental appliance present in FIGS. 2A and 2B, in accordance with certain non-limiting embodiments of the present technology.

With reference to FIG. 3, there is depicted an example configuration of an unfinished aligner 300 used for producing the aligner 10, in accordance with certain non-limiting embodiments of the present technology.

As it can be appreciated from FIG. 3, the unfinished aligner 300 includes an excess portion 302 formed during the thermoforming, which thus needs to be removed in order to produce the aligner 10, the aligner 10 comprising an upper portion (in the orientation of FIG. 3) of the unfinished aligner 300. For example, according to certain non-limiting embodiments of the present technology, the unfinished aligner 300 may be trimmed by a cutting device along the cut line 304, as will be described below.

In order to form the aligner 10 of a predetermined quality level allowing, for example, for acceptable comfort of wearing by the subject during the orthodontic treatment, it may be required to ensure a smooth open edge of the channel 26 of the aligner 10. There may be desired regions of roughness in certain configurations of the aligner 10, such as striations or buffings, for example, separate from the smooth open edge of the channel 26. Failing to meet the smooth open edge requirement may result, for example, in the aligner 10, when worn on the lower teeth 16, causing discomfort to the subject—for example, irritation of the lower gingiva 18, which may affect subject's adherence to the orthodontic treatment.

However, a higher quality of cutting may be associated with a greater power consumption of the cutting device. For example, for producing a smoother open edge of the channel 26, a lower speed of cutting may be required, at which the cutting device may consequently consume more power, and vice versa. Further, using the cutting parameters for a thick portion of the aligner 10 compared to a thin portion of the aligner 10 may produce variation along the cut line 304, such as jagged and smooth portions.

Thus, certain non-limiting embodiments of the present technology are directed to more efficient methods and systems for manufacturing the aligner 10 including: receiving an aligner mold 3D representation of the aligner mold (not depicted) indicative of the given configuration of the lower arch form 20 at the respective stage of the orthodontic treatment; determining, based on the aligner mold 3D representation, an aligner thickness distribution within the aligner 10; generating, based on the aligner thickness distribution, an aligner 3D representation of the aligner 10; receiving data indicative of the cut line 304; and determining, based on the aligner 3D representation, a cut line thickness of the aligner 10 along the cut line 304 for further use for forming the aligner 10. Further, the methods and systems described herein may be directed to adjusting at least some parameters of the cutting device based on the cut line thickness, thereby balancing between a power consumption, or other parameter, of the cutting device and the quality of cut of the open edge of the channel 26 of the aligner 10.

How the aligner mold 3D representation may be received, in accordance with certain non-limiting embodiments of the present technology, will be described below with reference to FIGS. 4 to 6. How the aligner thickness distribution of the aligner 10 may be determined, in accordance with certain non-limiting embodiments of the present technology, will be described further below with reference to FIGS. 7 to 10.

System

Figure 4:
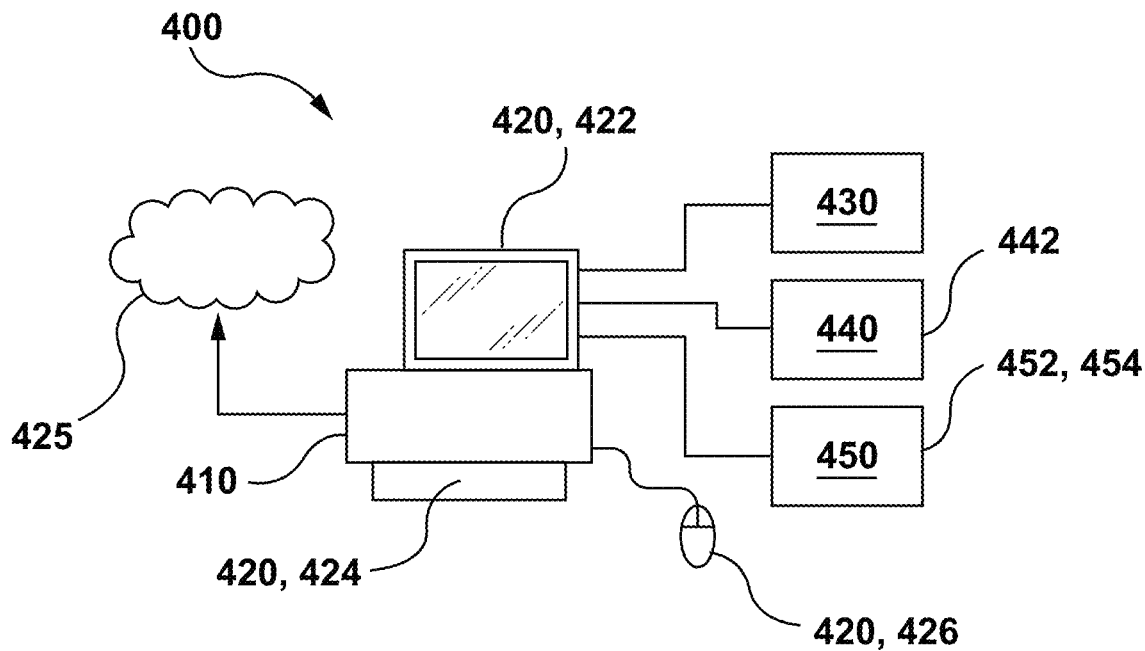
FIG. 4 depicts a schematic diagram of a system for determining the cut line depicted in FIG. 3 used for manufacturing the dental appliance of FIGS. 2A and 2B, in accordance with certain embodiments of the present technology.
Figure 5:
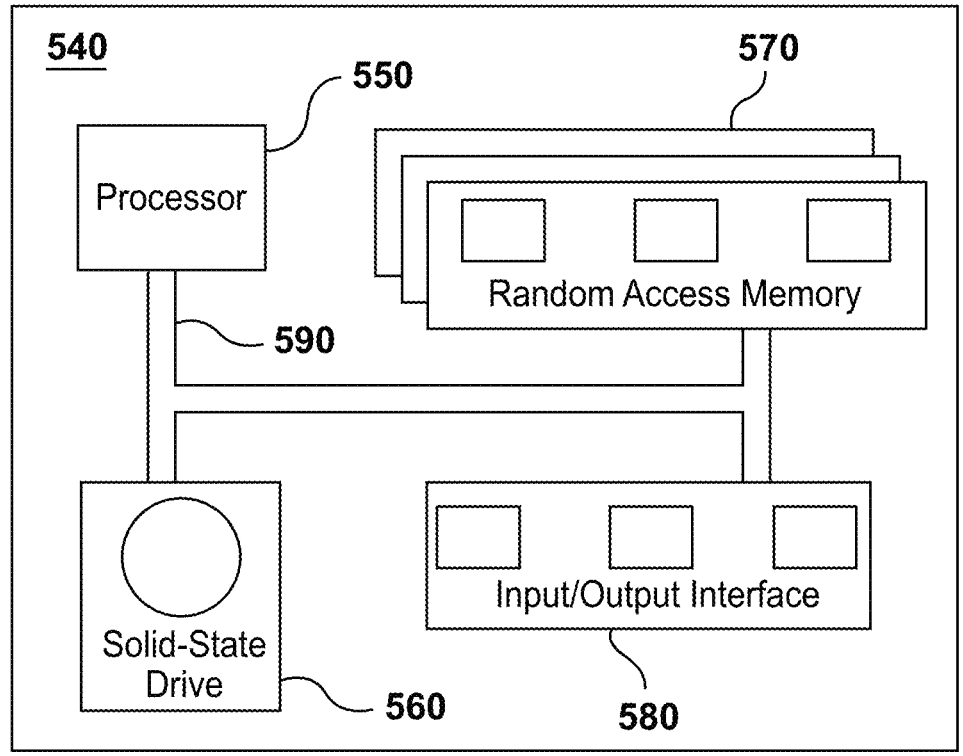
FIG. 5 depicts a schematic diagram of a computing environment of the system of FIG. 4, in accordance with certain embodiments of the present technology.

Referring to FIGS. 4 and 5, there is depicted a schematic diagram of a system 400 suitable for determining the aligner thickness distribution for producing the aligner 10, in accordance with certain non-limiting embodiments of the present technology.

It is to be expressly understood that the system 400 as depicted is merely an illustrative implementation of the present technology. Thus, the description thereof that follows is intended to be only a description of illustrative examples of the present technology. This description is not intended to define the scope or set forth the bounds of the present technology. In some cases, what is believed to be helpful examples of modifications to the system 400 may also be set forth below. This is done merely as an aid to understanding, and, again, not to define the scope or set forth the bounds of the present technology. These modifications are not an exhaustive list, and, as a person skilled in the art would understand, other modifications are likely possible. Further, where this has not been done (i.e., where no examples of modifications have been set forth), it should not be interpreted that no modifications are possible and/or that what is described is the sole manner of implementing that element of the present technology. As a person skilled in the art would understand, this is likely not the case. In addition, it is to be understood that the system 400 may provide in certain instances simple implementations of the present technology, and that where such is the case they have been presented in this manner as an aid to understanding. As persons skilled in the art would further understand, various implementations of the present technology may be of a greater complexity.

In certain non-limiting embodiments of the present technology, the system 400 of FIG. 4 comprises a computer system 410. The computer system 410 may be configured, by pre-stored program instructions, to determine, based on image data associated with the subject, such as the aligner mold 3D representation, the aligner thickness distribution of the aligner 10 for further forming it, for example, form the unfinished aligner 300. In additional non-limiting embodiments of the present technology, the computer system 410 may further be configured to cause applying the cut line 304 onto the unfinished aligner 300 and cause cutting, by the cutting device, the unfinished aligner 300, thereby forming the aligner 10 used for implementing the orthodontic treatment. In other non-limiting embodiments of the present technology, the computer system 410 may further be configured to cause cutting, by the cutting device, the unfinished aligner 300 along the cut line 304, thereby forming the aligner 10 used for implementing the orthodontic treatment. In other non-limiting embodiments of the present technology, the computer system 410 may further be configured to cause thermoforming, by a thermoforming system, a preform over a mold to generate the unfinished aligner 300.

To that end, in some non-limiting embodiments of the present technology, the computer system 410 may be configured to receive image data pertaining to the subject or to a given stage of the orthodontic treatment. According to some non-limiting embodiments of the present technology, the computer system 410 may receive the image data via local input/output interface (such as USB, as an example, not separately depicted). In other non-limiting embodiments of the present technology, the computer system 410 may be configured to receive the image data over a communication network 425, to which the computer system 410 is communicatively coupled.

In some non-limiting embodiments of the present technology, the communication network 425 is the Internet and/or an Intranet. Multiple embodiments of the communication network may be envisioned and will become apparent to the person skilled in the art of the present technology. Further, how a communication link between the computer system 410 and the communication network 425 is implemented will depend, inter alia, on how the computer system 410 is implemented, and may include, but is not limited to, a wire-based communication link and a wireless communication link (such as a Wi-Fi communication network link, a 3G/4G communication network link, and the like).

It should be noted that the computer system 410 can be configured for receiving the image data from a vast range of devices. Some of such devices can be used for capturing and/or processing data pertaining to maxillofacial and/or cranial anatomy of the subject. In certain embodiments, the image data received from such devices is indicative of properties of anatomical structures of the subject, including: teeth, intraoral mucosa, maxilla, mandible, temporomandibular joint, and nerve pathways, among other structures. In some non-limiting embodiments of the present technology, at least some of the image data is indicative of properties of external portions of the anatomical structures, for example dimensions of a gingival sulcus, and dimensions of an external portion of a tooth (e.g., a crown of the tooth) extending outwardly of the gingival sulcus. In some embodiments, the image data is indicative of properties of internal portions of the anatomical structures, for example volumetric properties of bone surrounding an internal portion of the tooth (e.g., a root of the tooth) extending inwardly of the gingival sulcus. Under certain circumstances, such volumetric properties may be indicative of periodontal anomalies which may be factored into an orthodontic treatment plan. In some non-limiting embodiments of the present technology, the image data includes cephalometric image datasets. In some embodiments, the image data includes datasets generally intended for the practice of endodontics. In some embodiments, the image data includes datasets generally intended for the practice of periodontics.

For example, in some non-limiting embodiments of the present technology, the system 400 may be configured to receive image data indicative of the given configuration of the lower arch form 20, such as the aligner mold 3D representation used for producing the unfinished aligner 300, which is associated with the respective stage of the orthodontic treatment preliminarily determined for the subject. In specific non-limiting embodiments of the present technology, the orthodontic treatment may be determined (for example, by a processor 550 depicted in FIG. 5) as described in a co-owned U.S. Pat. No. 10,993,782-B1 issued on May 4, 2021, and entitled "SYSTEMS AND METHODS FOR DETERMINING A TOOTH TRAJECTORY"; a content of which is hereby incorporated by reference in its entirety.

In alternative non-limiting embodiments of the present technology, the computer system 410 may be configured to receive the image data associated with the subject directly from an imaging device 430 communicatively coupled thereto. Broadly speaking, the processor 550 may be configured to cause the imaging device 430 to capture and/or process the image data of the lower teeth 16 and the periodontium (not depicted) of the subject. In certain non-limiting embodiments of the present technology, the image data may include, for example, one or more of: (1) images of external surfaces of respective crown portions of the lower teeth 16, (2) images of an external surface of the periodontium including those of the lower gingiva 18, the alveolar mandibular bone (not depicted), and images of superficial blood vessels and nerve pathways associated with the lower teeth 16; and (3) images of an oral region. By doing so, the imaging device 430 may be configured, for example, to capture image data of the lower arch form 20 of the subject. In another example, the imaging device may also be configured to capture and/or process image data of an upper arch form (not depicted) associated with the subject without departing from the scope of the present technology. It should be noted that the image data may include two-dimensional (2D) data and/or three-dimensional data (3D). Further, in certain non-limiting embodiments of the present technology, the image data includes 2D data, from which 3D data may be derived, and vice versa.

In some non-limiting embodiments of the present technology, the imaging device 430 may comprise a desktop scanner enabling to digitize the aligner mold (not depicted) representing the given configuration of the lower arch form 20 associated with the respective stage of the orthodontic treatment, thereby generating the aligner mold 3D representation for the aligner 10. In this regard, the aligner mold may have been obtained via dental impression using a material (such as a polymer, e.g. polyvinyl-siloxane) having been imprinted with the shape of the intraoral anatomy it has been applied to. In the dental impression, a flowable mixture (i.e., dental stone powder mixed with a liquid in certain proportions) may be flowed such that it may, once dried and hardened, form the replica.

In a specific non-limiting example, the desktop scanner can be of one of the types available from Dental Wings, Inc. of 2251, ave Letourneux, Montréal (QC), Canada, H1V 2N9. It should be expressly understood that the desktop scanner can be implemented in any other suitable equipment.

Further, it is contemplated that the computer system 410 may be configured for processing of the received image data. The resulting image data of the lower arch form 20 received by the computer system 410 is typically structured as a binary file or an ASCII file, may be discretized in various ways (e.g., point clouds, polygonal meshes, pixels, voxels, implicitly defined geometric shapes), and may be formatted in a vast range of file formats (e.g., STL, OBJ, PLY, DICOM, and various software-specific, proprietary formats). Any image data file format is included within the scope of the present technology. For implementing functions described above, the computer system 410 may further comprise a corresponding computing environment.

Further, in certain non-limiting embodiments of the present technology, the system 400 may be configured to receive data indicative of the cut line 304 and mark the cut line 304 on the unfinished aligner 300. To that end, the system 400 may further comprise a marking subsystem 440. It is not limited how the marking subsystem 440 may be implemented; however, in various non-limiting embodiments of the present technology, the marking subsystem 440 may include a marking head 442 for applying the cut line 304 onto the unfinished aligner 300 and a first robotic arm (not depicted) for holding and manipulating the unfinished aligner 300 around the marking head 442. In some non-limiting embodiments of the present technology, the marking head 442 may further comprise a coloring material storage (not depicted) for storing a coloring material (such as ink, as an example) and a supply control block (not depicted). In some non-limiting embodiments of the present technology, the marking head 442 may be implemented as a laser apparatus configurable to scorch the cut line 304 on the unfinished aligner 300.

In certain non-limiting embodiments of the present technology, the system 400 may further be configured to detect the cut line 304 applied on the unfinished aligner 300 and cut along the cut line to produce the aligner 10. In this regard, the system 400 may further comprise a forming subsystem 450. In some non-limiting embodiments of the present technology, the forming subsystem 450 may include a second robotic arm (not depicted), at an end-effector of which there is installed a camera device 452. In some non-limiting embodiments of the present technology, the camera device 452 can be any appropriate digital camera configured to detect the cut line 304 applied by the marking subsystem 440 described above onto the unfinished aligner 300, including, for example, but not limited to, a coupled-charged device camera (a CCD camera). Further, as mentioned above, the forming subsystem 450 may include the cutting device 454. Non limiting examples of the cutting device 454 may include a laser-based cutting device, a mechanical cutting device such as using a blade with a rotary or linear cutting action, and a water-jet based cutting device, as an example.

In some non-limiting embodiments of the present technology, both the marking subsystem 440 and the forming subsystem 450 of the system 400 may be implemented as described in a co-owned U.S. patent application Ser. No. 16/704,718 filed on Dec. 5, 2019, entitled "SYSTEMS AND METHODS FOR FORMING PERSONALIZED DENTAL APPLIANCES", the content of which is hereby incorporated by reference in its entirety Thus, the forming subsystem 450 may be configured to: (1) cause the camera device 452 to move around the unfinished aligner 300 with the cut line 304 applied thereon to detect the cut line 304 and generating respective image data thereof; (2) receive the image data of the cut line 304; and (3) based on the received image data of the cut line 304, cause cutting, by the cutting device 454 the unfinished aligner 300 along the cut line 304, thereby forming the aligner 10.

In other non-limiting embodiments of the present technology, the forming subsystem 450 may be configured for cutting the unfinished aligner 300 without requiring detection of the cut line 304. Instead, the determined cut line 304 is used to guide the cutting—for example, based on received data indicative of a position of the cut line 304 within the unfinished aligner 300. In some non-limiting embodiments of the present technology, the data indicative of the position of the cut line 304 within the unfinished aligner 300 may include at least one of: Cartesian coordinates; angular data indicative of a cutting angle for cutting the unfinished aligner 300; and a distance from the cutting device 454, as an example.

Further, with reference to FIG. 5, there is depicted a schematic diagram of a computing environment 540 suitable for use with some implementations of the present technology. The computing environment 540 comprises various hardware components including one or more single or multi-core processors collectively represented by the processor 550, a solid-state drive 560, a random-access memory 570 and an input/output interface 580. Communication between the various components of the computing environment 540 may be enabled by one or more internal and/or external buses 590 (e.g. a PCI bus, universal serial bus, IEEE 1394 "Firewire" bus, SCSI bus, Serial-ATA bus, ARINC bus, etc.), to which the various hardware components are electronically coupled.

The input/output interface 580 allows enabling networking capabilities such as wire or wireless access. As an example, the input/output interface 580 comprises a networking interface such as, but not limited to, a network port, a network socket, a network interface controller and the like. Multiple examples of how the networking interface may be implemented will become apparent to the person skilled in the art of the present technology. For example, but without being limiting, the input/output interface 580 may implement specific physical layer and data link layer standard such as Ethernet™, Fibre Channel, Wi-Fi™ or Token Ring™. The specific physical layer and the data link layer may provide a base for a full network protocol stack, allowing communication among small groups of computers on the same local area network (LAN) and large-scale network communications through routable protocols, such as IP.

According to implementations of the present technology, the solid-state drive 560 stores program instructions suitable for being loaded into the random-access memory 570 and executed by the processor 550, according to certain aspects and embodiments of the present technology. For example, the program instructions may be part of a library or an application.

In some non-limiting embodiments of the present technology, the computing environment 540 is implemented in a generic computer system, which is a conventional computer (i.e. an "off the shelf" generic computer system). The generic computer system may be a desktop computer/personal computer, but may also be any other type of electronic device such as, but not limited to, a laptop, a mobile device, a smart phone, a tablet device, or a server.

As persons skilled in the art of the present technology may appreciate, multiple variations as to how the computing environment 540 can be implemented may be envisioned without departing from the scope of the present technology.

Referring back to FIG. 4, the computer system 410 has at least one interface device 420 for providing an input or an output to a user of the system 400, the interface device 420 being in communication with the input/output interface 580. In the embodiment of FIG. 4, the interface device is a screen 422. In other non-limiting embodiments of the present technology, the interface device 420 may be a monitor, a speaker, a printer or any other device for providing an output in any form such as an image form, a written form, a printed form, a verbal form, a 3D model form, or the like.

In the depicted embodiments of FIG. 4, the interface device 420 also comprises a keyboard 424 and a mouse 426 for receiving input from the user of the system 400. Other interface devices 420 for providing an input to the computer system 410 can include, without limitation, a USB port, a microphone, a camera or the like.

The computer system 410 may be connected to other users, such as through their respective clinics, through a server (not depicted). The computer system 410 may also be connected to stock management or client software which could be updated with stock when the orthodontic treatment has been determined and/or schedule appointments or follow-ups with clients, for example.

Image Data

As alluded to above, according to certain non-limiting embodiments of the present technology, the processor 550 may be configured to: (1) receive image data indicative of the given configuration of an internal surface of the aligner 10 corresponding to the respective stage of the orthodontic treatment; (2) determine, based on the image data, the aligner thickness distribution after manufacture; and (3) generate, based on the aligner thickness distribution, the aligner 3D representation further used for producing the aligner 10.

Figure 6:
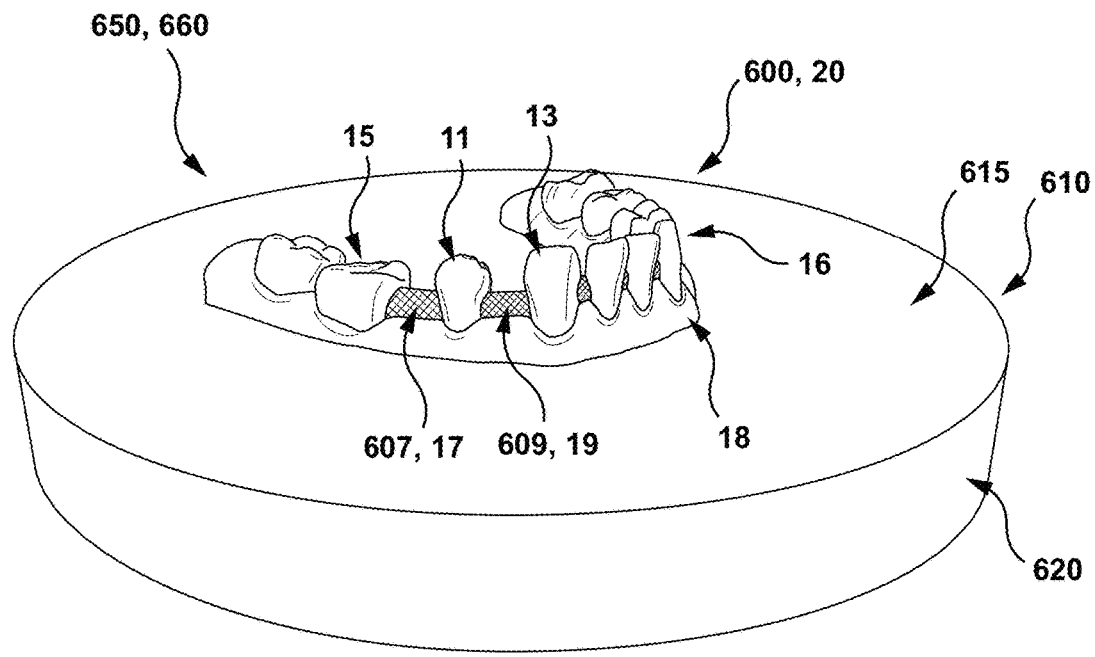
FIG. 6 depicts a 3D model of a given configuration of the lower arch form used for manufacturing the dental appliance of FIGS. 2A and 2B, the 3D model including a 3D representation of a support surface used for manufacturing the dental appliance of FIGS. 2A and 2B, in accordance with certain non-limiting embodiments of the present technology.

With reference to FIG. 6, there is depicted a perspective view of an aligner mold 3D representation 600 representative of the inner surface 12 of the aligner 10 used for producing the unfinished aligner 300, in accordance with certain non-limiting embodiments of the present technology.

For example, in some non-limiting embodiments of the present technology, the unfinished aligner 300 may be produced via thermoforming the preform on the aligner mold, produced based on the aligner mold 3D representation 600, as described above. Thus, the aligner mold 3D representation 600 may thus be determined as being representative of the inner surface 12 of the aligner 10 described above.

According to certain non-limiting embodiments of the present technology, the aligner mold 3D representation 600 may comprise tooth 3D representations of the lower teeth 16, such as those of the first tooth 11, the second tooth 13, and the third tooth 15; and a gingiva 3D representation (not separately labelled) of the lower gingiva 18.

It should be expressly understood that, the description herein below is provided with respect to the lower arch form 20 of the subject (and associated therewith the lower teeth 16 and the lower gingiva 18) for the sake of clarity and simplicity thereof, and in no way as a limitation. It will be appreciated that the non-limiting embodiments of the present technology can also apply to the upper teeth of the upper arch form (both not depicted) with certain alterations, which will be explicitly indicated below where necessary.

Further, in accordance with certain non-limiting embodiments of the present technology, the processor 550 may be configured to generate the aligner mold 3D representation 600 comprising a plurality of mesh elements representative of the inner surface 12 of the aligner 10. In certain non-limiting embodiments of the present technology, the plurality of mesh elements may be represented, without limitation, by triangular mesh elements, quadrilateral mesh elements, convex polygonal mesh elements, or even concave polygonal mesh elements, as an example, without departing from the scope of the present technology.

Further, as it can be appreciated from FIG. 6, in some non-limiting embodiments of the present technology, the aligner mold 3D representation 600 may further include at least one, so called, interdental filler model—such as a first interdental filler model 607 associated with the first interdental space 17 and a second interdental filler model 609 associated with the second interdental space 19.

In the context of the present specification, a given interdental bridge, such as the first interdental filler model 607, denotes a surface extending within the first interdental space 17 in a mesiodistal direction, thereby filling it in. According to certain non-limiting embodiments of the present technology, the first interdental filler model 607 may have an arch-like profile in a linguolabial section thereof grounded in the gingiva 3D representation within the first interdental space 17.

According to certain non-limiting embodiments of the present technology, each one of the first interdental filler model 607 and the second interdental filler model 609 may be used for generating respective interdental fillers, which may be used as separate orthodontic appliances providing support to the aligner 10 when it worn on the lower teeth 16. In other non-limiting embodiments of the present technology, the aligner mold 3D representation 600 including each one of the first interdental filler model 607 and the second interdental filler model 609 may be used for producing the aligner 10, which would be free of contact with the lower gingiva 18 when it is worn on the lower teeth 16.

In some non-limiting embodiments of the present technology, the processor 550 may be further configured to obtain the first interdental filler model 607. For example, the first interdental filler model 607 may be generated by third-party software based on the aligner mold 3D representation 600 and stored in a data format receivable by the processor 550.

However, in other non-limiting embodiments of the present technology, the processor 550 may be configured to determine the first interdental filler model 607 by applying one or more approaches described in a co-owned U.S. patent application Ser. No. 17/143,033 filed Jan. 6, 2021, and entitled "METHOD AND SYSTEM FOR GENERATING INTERDENTAL FILLER MODELS"; the content of which is hereby incorporated by reference in its entirety.

More specifically, in certain non-limiting embodiments of the present technology, in order to determine the first interdental filler model 607, the processor 550 may be configured to: (i) receive the aligner mold 3D representation 600 including a plurality of individual segmentation loops, each one of the plurality of individual segmentation loops indicative of a boundary between a respective one of the lower teeth and the lower gingiva 18 within the aligner mold 3D representation 600; (ii) determine locations for ends of the first interdental filler model 607 between the first tooth 11 and the second tooth 13 by: determining a first vertex on a tooth axis associated with first tooth 11, and determining a second vertex on a tooth axis of the second tooth 13; (iii) determine a curvature of the first interdental filler model 607 by: determining a first arc connecting the first vertex to the second vertex; (iv) determine a shape of the first interdental filler model 607 by: determining a second arc having a center at the first vertex, determining a third arc having a center at the second vertex, and interpolating a set of arcs between the second arc and the third arc, wherein a center of each arc in the set of arcs corresponds to a vertex on the first arc; (v) ground the first interdental filler model 607 on the gingiva 3D representation by: extending each arc of the set of arcs to end on a ground surface; and (vi) generate the first interdental filler model 607 by: connecting free ends of each arc of the set of arcs, thereby forming a set of sections, lofting each section of the set of sections, and forming the first interdental filler model 607 based on the set of sections.

Further, as can be appreciated from FIG. 6, the aligner mold 3D representation 600 may be positioned on a support surface 3D representation 610 indicative of a surface, on which the aligner mold is to be positioned during the producing the thermoforming the unfinished aligner 300 as depicted in FIG. 6. For example, the support surface 3D representation 610 may be representative of a vacuum chamber table of a thermoforming chamber used for producing the aligner 10. To that end, the support surface 3D representation 610 may have a cylindrical form further including a base portion 615 and a generatrix portion 620.

In some non-limiting embodiments of the present technology, the processor 550 may be configured to receive the aligner mold 3D representation 600 and the support surface 3D representation 610 as a single 3D mesh 650, as depicted in FIG. 6. In this regard, the single 3D mesh 650 may be defined by a plurality of inner vertices 660 of the aligner mold 3D representation 600 and the support surface 3D representation 610.

In other non-limiting embodiments of the present technology, the processor 550 may be configured to generate the single 3D mesh 650 based on the aligner mold 3D representation 600 and the support surface 3D representation 610 received as separate meshes, and further combine them into the single 3D mesh 650.

According to certain non-limiting embodiments of the present technology, the processor 550 may be configured to determine the aligner thickness distribution based on the single 3D mesh 650, as will be described below with reference to FIGS. 7 to 10.

Determining Aligner Thickness Distribution

According to certain non-limiting embodiments of the present technology, the processor 550 may be configured to determine the aligner thickness distribution based on respective distances from each one of the plurality of inner vertices 660 defining the single 3D mesh 650 to a cover surface generated, by the processor 550, to encompass a totality of the plurality of inner vertices 660 therewithin.

Figure 7:
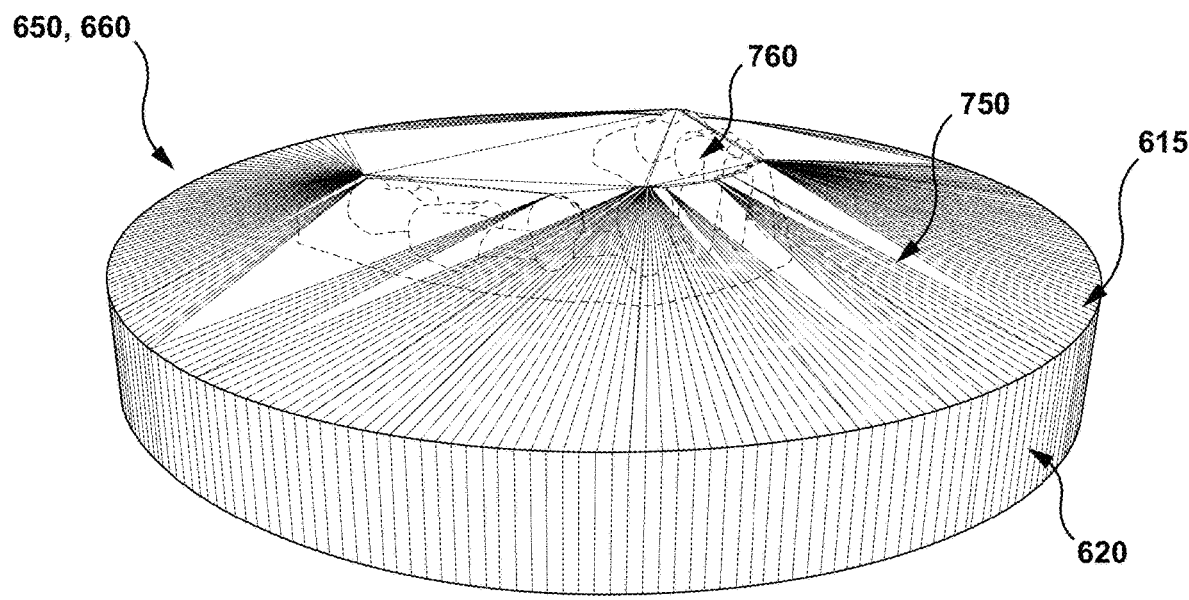
FIG. 7 depicts a schematic diagram of a step for generating, by a processor of FIG. 5, a cover surface around the 3D model for determining a thickness distribution within the orthodontic appliance of FIGS. 2A and 2B, in accordance with certain non-limiting embodiments of the present technology.

With reference to FIG. 7, there is depicted an example of a cover surface 750 generated, by the processor 550, to encompass the plurality of inner vertices 660 of the single 3D mesh 650, in accordance with certain non-limiting of the present technology.

According to certain non-limiting embodiments of the present technology, the processor 550 may be configured to generate the cover surface 750 based on a predetermined reference plane, such as a reference plane 760. It is not limited how the reference plane 760 is determined; however, in some non-limiting embodiments of the present technology, the processor 550 may be configured to generate the reference plane 760 according to a predetermined position thereof relative to the single 3D mesh 650.

For example, in some non-limiting embodiments of the present technology, the reference plane 760 may be generated to be inclined to the base portion 615 of the support surface 3D representation 610 at a predetermined angle—such as 3, 5, or 10 degrees, as an example. Thus, the reference plane 760 may be spaced from at least some of the plurality of inner vertices 660. In these embodiments, the at least some of the plurality of inner vertices 660 may be those that are representative of occlusal surfaces of some of the lower teeth 16, as an example.

In other non-limiting embodiment of the present technology, the processor 550 may be configured to generate the reference plane 760 to extend through at least some of the plurality of inner vertices 660. In specific non-limiting embodiments of the present technology, the reference plane 760 may extend through outermost ones of the plurality of inner vertices 660 representative of the occlusal surfaces of respective ones of the lower teeth 16.

Further, in some non-limiting embodiments of the present technology, the processor 550 may be configured to generate planes adjacent to the reference plane 760 such that the so-generated adjacent planes extend through other outermost ones of the plurality of inner vertices 660. Further, the processor 550 may be configured to iteratively determine other planes adjacent to previously generated ones and extending through respective outermost ones of the plurality of inner vertices 660, until the totality of the plurality of inner vertices 660 is encompassed within so generated planes. Thus, by so doing, in accordance with certain non-limiting embodiments of the present technology, the processor 550 may be configured to generate the cover surface 750.

In specific non-limiting embodiments of the present technology, the processor 550 may be configured to generate the cover surface 750, based on the reference plane 760, applying a Quick Hull algorithm. It should be expressly understood that other algorithms and techniques for generating the cover surface 750 around the plurality of inner vertices 660 can also be envisioned without departing from the scope of the present technology.

Figure 8:
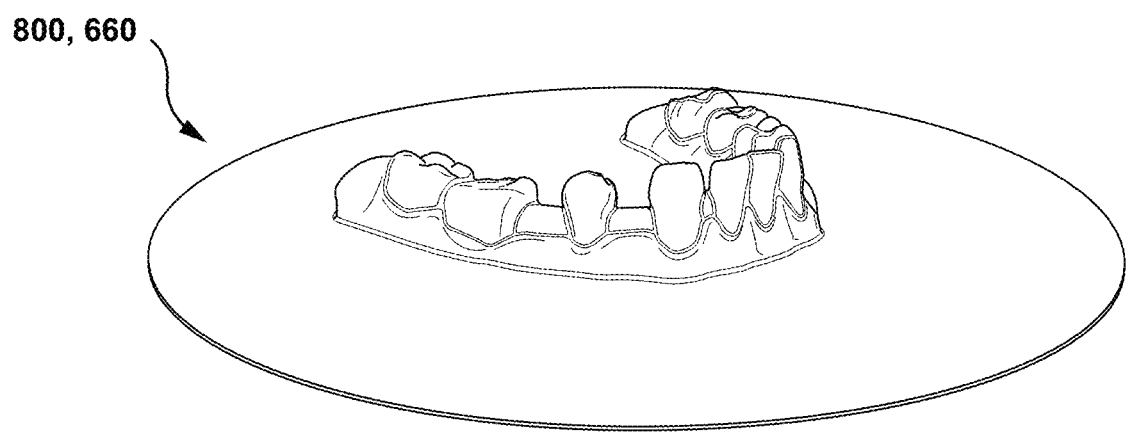
FIG. 8 depicts a 3D representation of a mold of an unfinished orthodontic appliance generated, by the processor of FIG. 5, for determining the thickness distribution within the orthodontic appliance of FIGS. 2A and 2B, according to certain embodiments of the present technology.

In additional non-limiting embodiments of the present technology, after generating the cover surface 750, the processor 550 may be configured to remove those of the plurality of inner vertices 660 representative of the generatrix portion 620 of the support surface 3D representation 610. By so doing, the processor 550 may be configured to generate an unfinished aligner mold 3D representation 800 representative of an inner surface of the unfinished aligner 300 as depicted in FIG. 8, in accordance with certain non-limiting embodiments of the present technology.

Further, in accordance with certain non-limiting embodiments of the present technology, the processor 550 may be configured to use the unfinished aligner mold 3D representation 800 to determine the respective distances from each one of the plurality of inner vertices 660 to the cover surface 750, as will be described below.

Figure 9A:
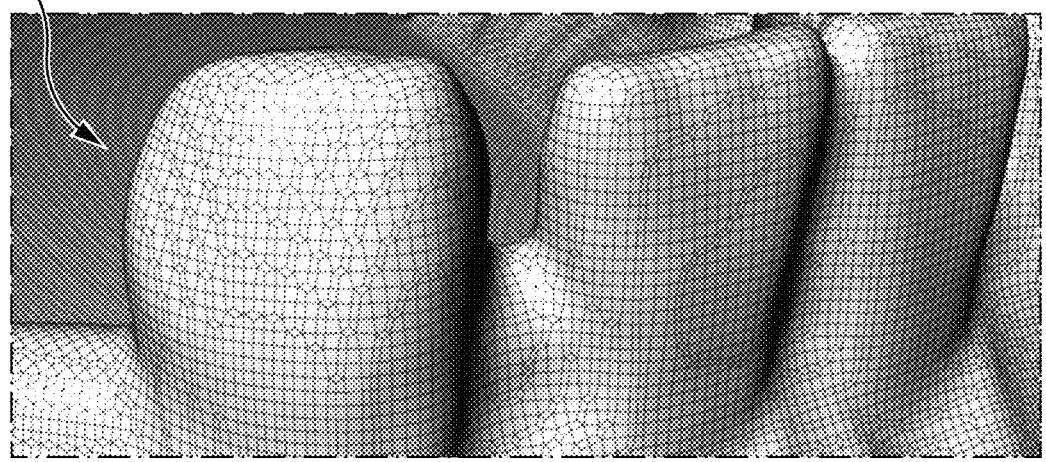
FIGS. 9A and 9B depict a step for re-meshing, by the processor of FIG. 5, a surface of the 3D representation of the mold of the unfinished orthodontic appliance of FIG. 8 determining the thickness distribution within the orthodontic appliance of FIGS. 2A and 2B.

However, without additional processing, the plurality of inner vertices 660 may be chaotically scattered within the unfinished aligner mold 3D representation 800—such as represented by a raw distribution 902 of the plurality of inner vertices 660 depicted in FIG. 9A, in accordance with certain non-limiting embodiments of the present technology. As will become apparent from the description provided herein below, using the plurality of inner vertices 660 distributed according to the raw distribution 902 may result in the aligner thickness distribution being unevenly determined within the unfinished aligner 3D representation 800, which may not provide sufficient information of the thickness of the aligner 10 needed for manufacture thereof.

Thus, prior to determining the respective distances, according to some non-limiting embodiments of the present technology, the processor 550 may be configured to re-mesh a surface of the unfinished aligner mold 3D representation 800 to redistribute the plurality of inner vertices 660 within the unfinished aligner mold 3D representation 800 uniformly.

To that end, the processor 550 may be configured to re-mesh the surface of the unfinished aligner mold 3D representation 800 using mesh elements that would, for example, meet at least one of the following non-exhaustive criteria: (1) the mesh elements have an equal edge length; (2) the mesh elements are distributed within the unfinished aligner mold 3D representation 800 with a predetermined valence, that is, each mesh element has a predetermined number of adjacent thereto mesh elements (such as six in case of triangular mesh elements, as an example); and (3) the mesh elements preserve geometric features of the unfinished aligner mold 3D representation 800, such as following a curvature of the unfinished aligner mold 3D representation 800.

Thus, in some non-limiting embodiments of the present technology, the processor 550 may be configured to convert the unfinished aligner mold 3D representation 800 into a voxel space. Further, using quadrilateral mesh elements obtained in the voxels space, the processor 550 may be configured to re-mesh the surface of the unfinished aligner mold 3D representation 800.

In other non-limiting embodiments of the present technology, the processor 550 may be configured to use other isotropic mesh elements, such as triangular or polygonal isotropic mesh elements, each one of which has, aside from the above-listed properties, a regular shape within the unfinished aligner 3D representation 800. For example, an isotropic triangular mesh element may be an equilateral triangle, and an isotropic polygonal mesh element may be a regular hexagon.

Figure 9B:
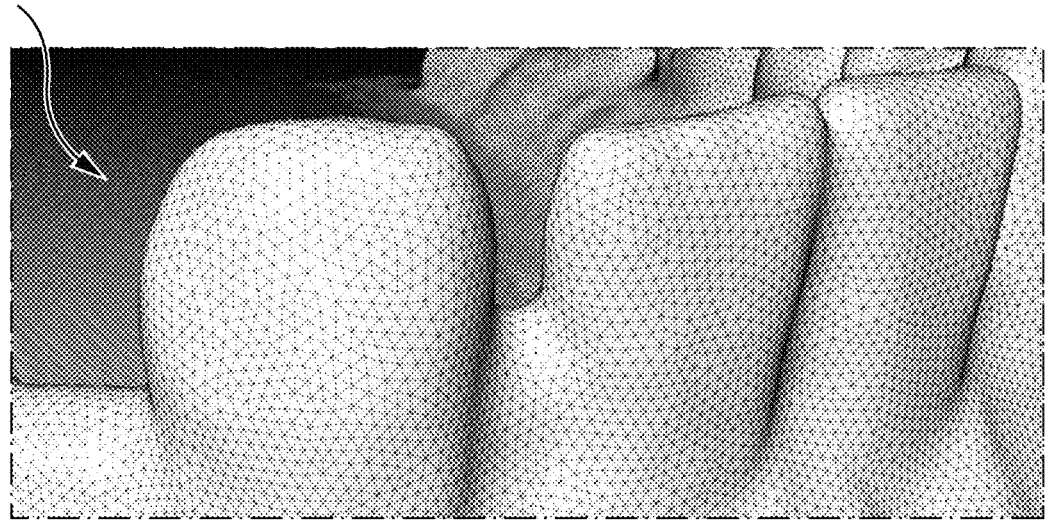

Thus, the processor may be configured to generate a uniform distribution 904 of the plurality of inner vertices 660 within the unfinished aligner mold 3D representation 800 as depicted in FIG. 9B, in accordance with certain non-limiting embodiments of the present technology.

Figure 10A:
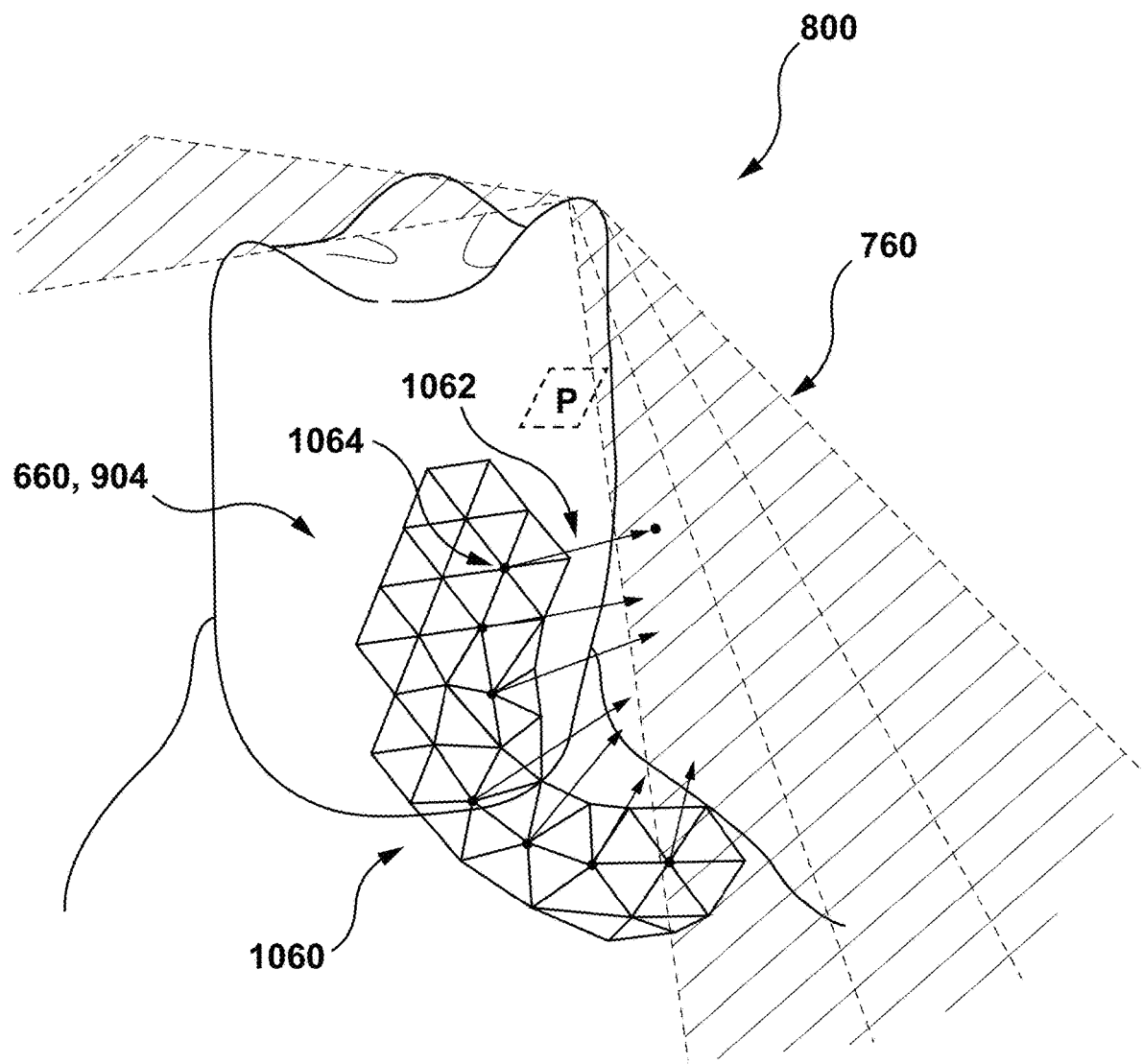
FIGS. 10A and 10B depict a schematic diagram of a step for determining, by the processor of FIG. 5, respective distances between each vertex of the 3D representation of the mold of the unfinished aligner of FIG. 9B and the cover surface of FIG. 7, indicative of the thickness distribution within the orthodontic appliance of FIGS. 2A and 2B, in accordance with certain non-limiting embodiments of the present technology.

Further, with reference to FIG. 10A, there is depicted a magnified view of the unfinished aligner mold 3D representation 800 covered by the cover surface 750 illustrating a step for determining, by the processor 550, the respective distances from each one of the plurality of inner vertices 660 to the cover surface 750, in accordance with certain non-limiting embodiments of the present technology.

According to certain non-limiting embodiments of the present technology, the processor 550 may be configured to determine the respective distances along respective normal vectors determined therein—such as a plurality of normal vectors 1060. It should be expressly understood that how the processor 550 can be configured to determine the plurality of normal vectors 1060 associated with the plurality of inner vertices 660 is not limited, and, typically, may include analyzing spatial positions of associated edges of respective mesh elements, face normal vectors associated therewith (not depicted), and the like. In this regard, the processor 550 may be configured to apply one of the following inexhaustive list of techniques to determine a given normal vector 1062 at a respective inner vertex 1064 of the plurality of inner vertices 660: a mean weighted equality algorithm, a mean weighted by angle algorithm, a mean weighted by sine and edge length reciprocal algorithm, a mean weighted by areas of adjacent mesh elements, and the like. Details of implementation of some of these algorithms may be obtained, for example, from an article titled "*A Comparison of Algorithms for Vertex Normal Computation*" written by Shuangshuang Jin, Robert R. Lewis, David West, and published by Washington State University, the content of which is incorporated herein by reference in its entirety.

Further, the processor 550 may be configured to determine a given distance p from the respective inner vertex 1064 to the cover surface 750 along the given normal vector 1062. Thus, according to certain non-limiting embodiments of the present technology, the processor 550 may be configured to determine the respective distances from each one of the plurality of inner vertices 660 of the unfinished aligner mold 3D representation 800 to the cover surface 750, which may thus be representative of the aligner thickness distribution of the aligner 10.

Further, in some non-limiting embodiments of the present technology, the processor 550 may be configured to visualize the respective distances associated with the plurality of inner vertices 660 on the unfinished aligner 3D representation 800, and further cause display of the unfinished aligner mold 3D representation 800 in the screen 422 of the computer system 410. It should be noted that visualization techniques that may be used within the scope of the present technology for representing the respective distances on the unfinished aligner mold 3D representation 800 are not limited and may include various diagrams and charts representative of changes in clearance between the surface of the unfinished aligner mold 3D representation 800 and the cover surface 750.

Figure 10B:
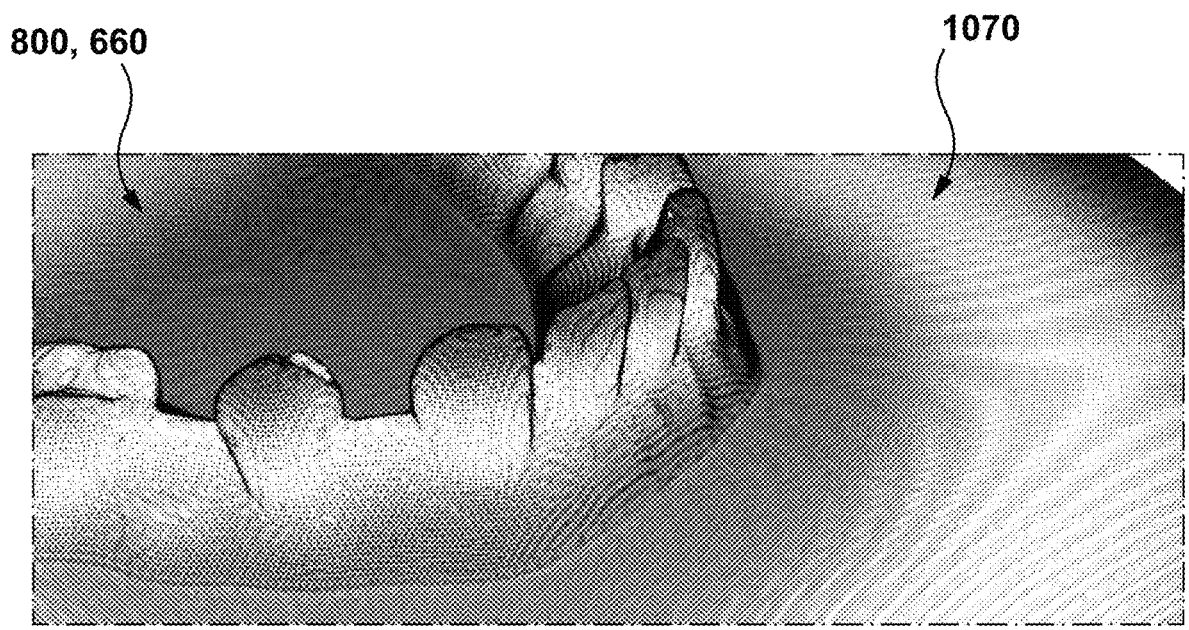

However, in specific non-limiting embodiments of the present technology, the processor 550 may be configured to generate a heat map representation of the respective distances, such as a heat map representation 1070 schematically depicted in FIG. 10B, in accordance with certain non-limiting embodiments of the present technology.

In some non-limiting embodiments of the present technology, the heat map representation 1070 may be a monochromatic heat map representation where greater values of the respective distances associated with the plurality of inner vertices 660 are assigned greater intensity values of a given color, and vice versa. In other non-limiting embodiments of the present technology, the heat map representation 1070 may be a polychromatic heat map representation associated with a predetermined color spectrum including at least two colors. In this example, the greater values of the respective distances are assigned respective colors closer to a lower boundary of the predetermined color spectrum (being a green color, for example), and smaller values of the respective distances are assigned colors closer a higher boundary (being a red color, for example) of the predetermined color spectrum.

In additional non-limiting embodiments of the present technology, the processor 550 may be configured to store the heat map representation 1070 in one of the solid-state drive 560 and the random access memory 570 for further causing display thereof in the screen 422.

Further, in some non-limiting embodiments of the present technology, the processor 550 may be configured to determine, based on the respective distances, respective thickness values of the aligner 10 associated with each one of the plurality of inner vertices 660, thereby determining the aligner thickness distribution of the aligner 10.

To that end, the processor 550 may be configured to determine the respective thickness values based on a configuration and physical properties of the preform used for thermoforming the aligner 10. More specifically, in some non-limiting embodiments of the present technology, based on the given distance p, the processor 550 may be configured to determine a respective thickness value of the aligner 10 associated with the respective inner vertex 1064 according to the following equation:

$$\|n\| = h - kp, \quad (1)$$

where $\|n\|$ is the given thickness value;
h is an initial thickness of the preform used for manufacturing the aligner 10;
k is a predetermined coefficient; and
p is the given distance associated with the respective inner vertex 1064.

In some non-limiting embodiments of the present technology, the predetermined coefficient k can be determined to meet a condition of volume constancy between the preform used for manufacturing the aligner 10 and the aligner 10 itself. In other words, the processor 550 may be configured to determine the predetermined coefficient k, such that the following condition is satisfied:

$$V_0 = V_f, \quad (2)$$

where $V_0$ is a volume of the preform; and
$V_f$ is a volume of the aligner 10 after the manufacturing.

Thus, according to certain non-limiting embodiments of the present technology, the processor 550 may be configured to determine the respective thickness values of the aligner thickness distribution of the aligner 10 at each one of the plurality of inner vertices 660.

Further, in accordance with certain non-limiting embodiments of the present technology, the processor 550 may be configured, based on the respective thickness values, to determine an outer surface of the unfinished aligner 300.

Figure 11A:
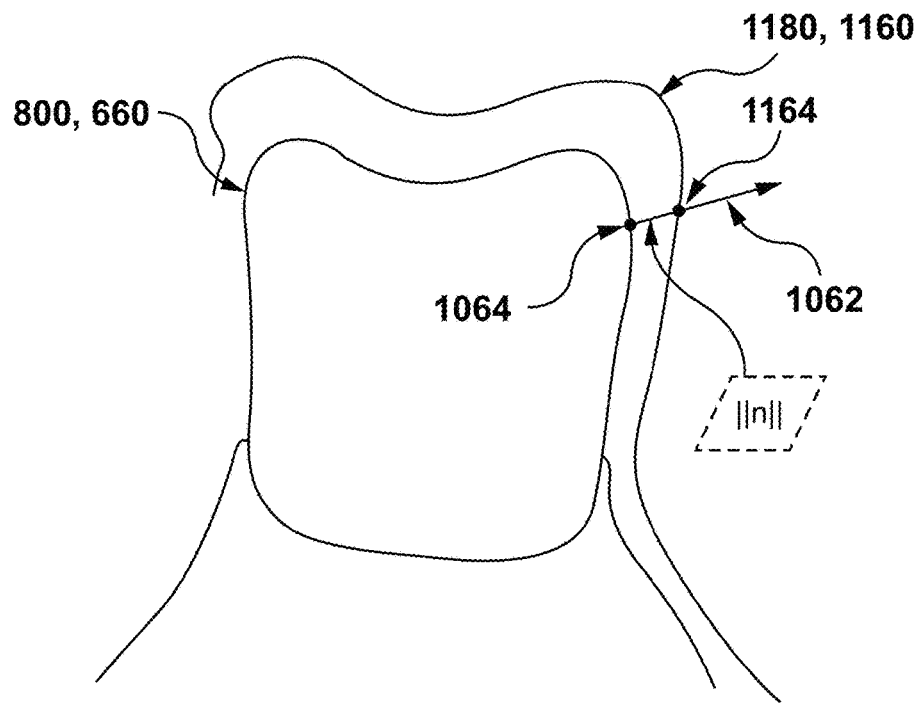
FIGS. 11A and 11B depict a schematic diagram of a step for generating a 3D representation of the orthodontic appliance of FIGS. 2A and 2B based on the thickness distribution thereof, in accordance with certain non-limiting embodiments of the present technology.

With reference to FIG. 11A, there is depicted a schematic diagram of a cross-section of a given portion of the unfinished aligner mold 3D representation 800 along a lingual-buccal plane illustrating a step for determining, by the processor 550, a plurality of outer vertices 1160 defining an unfinished aligner outer surface 1180 of the unfinished aligner 300, in accordance with certain non-limiting embodiments of the present technology.

In this regard, in some non-limiting embodiments of the present technology, the processor 550 may be configured to determine a given outer vertex 1164 of the plurality of outer vertices 1160 by offsetting the respective inner vertex 1064 at the given thickness value $\|n\|$, determined therein in accordance with Equation (1), along the given normal vector 1062 of the plurality of normal vectors 1060. Thus, by offsetting each one of the plurality of inner vertices 660 at a respective thickness value associated therewith in a direction of a respective one of the plurality of normal vectors 1060, the processor 550 may be configured to determine the plurality of outer vertices 1160 defining the unfinished aligner outer surface 1180 of the unfinished aligner 300.

Figure 11B:
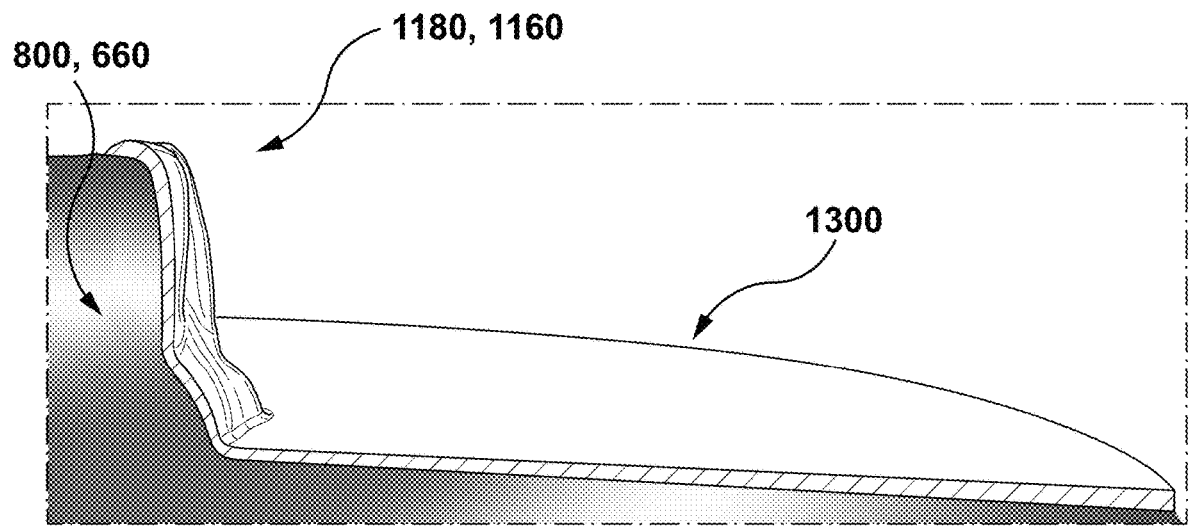

Further, in some non-limiting embodiments of the present technology, the processor 550 may be configured to generate, based on the plurality of inner vertices 660 and the plurality of outer vertices 1160, an unfinished aligner 3D representation 1300 of the unfinished aligner 300, depicted in FIG. 11B, in accordance with certain non-limiting embodiments of the present technology.

Thus, by generating the unfinished aligner 3D representation 1300 based on the aligner thickness distribution, the processor 550 may be said to simulate the thermoforming process of producing the aligner 10.

Manufacturing the Orthodontic Appliance

According to certain non-limiting embodiments of the present technology, using the unfinished aligner 3D representation 1300, the processor 550 may be configured to produce the aligner 10.

In some non-limiting embodiments of the present technology, where the aligner 10 is produced via the thermoforming process, using the unfinished aligner 3D representation 1300, the processor 550 may be configured to determine parameters of the forming subsystem 450 for cutting the unfinished aligner 300 (pre-manufactured based on the aligner mold as described above) along the cut line 304.

To that end, the processor 550 may be configured to: (1) obtain data indicative of a position of the cut line 304 within the unfinished aligner 300; (2) apply the data to the unfinished aligner 3D representation 1300; (3) based on the unfinished aligner 3D representation 1300, determine the cut line thickness of the aligner 10 along the cut line 304; and (4) based on the cut line thickness, determine the parameters of the forming subsystem 450 for cutting, by the cutting device 454, the unfinished aligner 300 along the cut line 304, thereby forming the aligner 10.

In some non-limiting embodiments of the present technology, the data indicative of the position of the cut line 304 may have been determined by third-party software based on an arch form 3D representation indicative of an actual configuration of the lower arch form 20 and stored in a data format receivable by the processor 550.

In other non-limiting embodiments of the present technology, the processor 550 may be configured to determine the data indicative of the position of the cut line 304 using one the approaches described in a co-owned U.S. Pat. No. 11,058,515-B1 issued on Jul. 13, 2021 and entitled "SYSTEMS AND METHODS FOR FORMING DENTAL APPLIANCES"; the content of which is hereby incorporated by reference in its entirety. More specifically, the processor 550 may be configured to: obtain the arch from 3D representation of the lower arch form 20; obtain, using the arch from 3D representation, for each one of the lower teeth 16, a respective one of a plurality of individual intersection loops, given one of the plurality of individual intersection loops being indicative of a boundary between a given one of the lower teeth and the lower gingiva 18; segment, based on a predetermined rule, each one of the plurality of individual intersection loops into a buccal portion and a lingual portion; sequentially join, respective buccal portions and respective lingual portions associated with each one of the plurality of individual intersection loops, thereby generating a single arch form loop; smooth the single arch form loop, thereby generating a smoothed single arch form loop; and determine the cut line 304 of the aligner 10 as the smoothed single arch form loop.

In some non-limiting embodiments of the present technology, the parameters of the forming subsystem 450 determined by the processor 550 for cutting may comprise parameters of the cutting device 454 associated with intensity of cutting, such as power, as an example.

In specific non-limiting embodiments of the present technology, the parameters associated with the intensity of cutting may include a speed of cutting. In this regard, the processor 550 may be configured to determine the speed of cutting such that: (1) it increases for cutting through portions of the unfinished aligner 300 having greater values of the cut line thickness; and (2) decreases for cutting through portions of the unfinished aligner 300 associated with smaller values of the cut line thickness. By so doing, the processor 550 may be configured, for example, to generate an array of speed values, each of which is associated with a respective value of the cut line thickness of the aligner 10 along the cut line 304. Thus, the array of speed values may be said to define a speed profile of cutting and may further be used, by the processor 550, to modulate the speed of cutting of the cutting device 454 when causing the cutting device 454 to trim the excess portion 302 from the unfinished aligner 300.

In other non-limiting embodiments of the present technology, where the cutting device 454 is one of the laser cutting device and the water-jet based cutting device, the parameters associated with intensity of cutting may comprises a distance between the cutting device 454 and the unfinished aligner 300. In these embodiments, the processor 550 may be configured to determine the distance between the cutting device 454 and the unfinished aligner 300 such that:

(1) it decreases for cutting through portions of the unfinished aligner 300 having greater values of the cut line thickness; and (2) on the other hand, the distance increases for cutting through portions having smaller values. Further, the processor 550 may be configured to generate an array of distance values, each of which is associated with the respective value of the cut line thickness of the aligner 10 along the cut line 304. Thus, using the array of distance values, the processor 550 may further be configured to modulate the distance between the cutting device 454 and the unfinished aligner 300 causing the cutting device 454 to move closer to or farther from the unfinished aligner 300 based on the cut line thickness.

Thus, the processor 550 may be configured to modulate the parameters of the cutting device 454 based on a trade-off between the consumed power of the cutting device 454 and a level of smoothness of thus produced open edge of the channel 26 of the aligner 10, thereby providing more optimized power consumption of the cutting device 454 while producing open edge of the channel 26 of the aligner 10 of a predetermined smoothness level.

For example, causing higher intensity of the cutting—by at least one of increasing the speed of cutting and decreasing the distance between the cutting device 454 and the unfinished aligner 300—through portions of the unfinished aligner 300 having greater values of the cut line thickness, the processor 550 may be configured to reduce such cutting defects of the open edge of the channel 26 as striations or buffings, as an example. In another example, causing lower intensity of the cutting—by at least one of decreasing the speed of cutting and increasing the distance between the cutting device 454 and the unfinished aligner 300—through portions of the unfinished aligner 300 having smaller values of the cut line thickness, the processor 550 may be configured to reduce such cutting defects as overburns (in the embodiments, where the cutting device 454 is one the laser cutting device and the mechanical cutting device) resulting in a charred open edge of the channel 26 of the aligner 10.

Further, in some non-limiting embodiments of the present technology, based on the so determined parameters of the cutting device 454, the processor 550 may be configured to cause the forming subsystem 450 to cut the unfinished aligner 300 along the cut line 304.

In those embodiments of the present technology where the cut line 304 has been preliminarily applied to the unfinished aligner 300, the processor 550 may be configured to cause the forming subsystem 450 to detect, by the camera device 452, the cut line 304 on the unfinished aligner 300 and cut, by the cutting device 454, therealong, thereby producing the aligner 10 for use by the subject in the course of the orthodontic treatment.

However, in other non-limiting embodiments of the present technology, where the cut line 304 has not been applied to the unfinished aligner 300, the processor 550 may be configured to cause the forming subsystem 450 to cut the unfinished aligner 300, for example, based on the data indicative of the position of the cut line 304 within the unfinished aligner 300. In some non-limiting embodiments of the present technology, the processor 550 may be configured to receive the data indicative of the position of the cut line 304 within the unfinished aligner 300 including at least one of: Cartesian coordinates and angular data indicative of a cutting angle for cutting the unfinished aligner 300, as an example.

More specifically, in some non-limiting embodiments of the present technology, in order to cause producing of the aligner 10 from the unfinished aligner 300, the processor 550 may be configured to apply one of the approaches described in the co-owned U.S. patent application Ser. No. 16/704,718 filed on Dec. 5, 2019, entitled "SYSTEMS AND METHODS FOR FORMING DENTAL APPLIANCES", the content of which is hereby incorporated by reference in its entirety.

In yet other non-limiting embodiments of the present technology, the processor 550 may be configured to generate, based on the data indicative of the position of the cut line 304, an aligner 3D representation (not depicted) of the aligner 10 from the unfinished aligner 3D representation 1300. Further, the processor 550 may be configured to cause producing the aligner 10 based on the aligner 3D representation (not depicted) using 3D printing techniques.

Method

Figure 12:
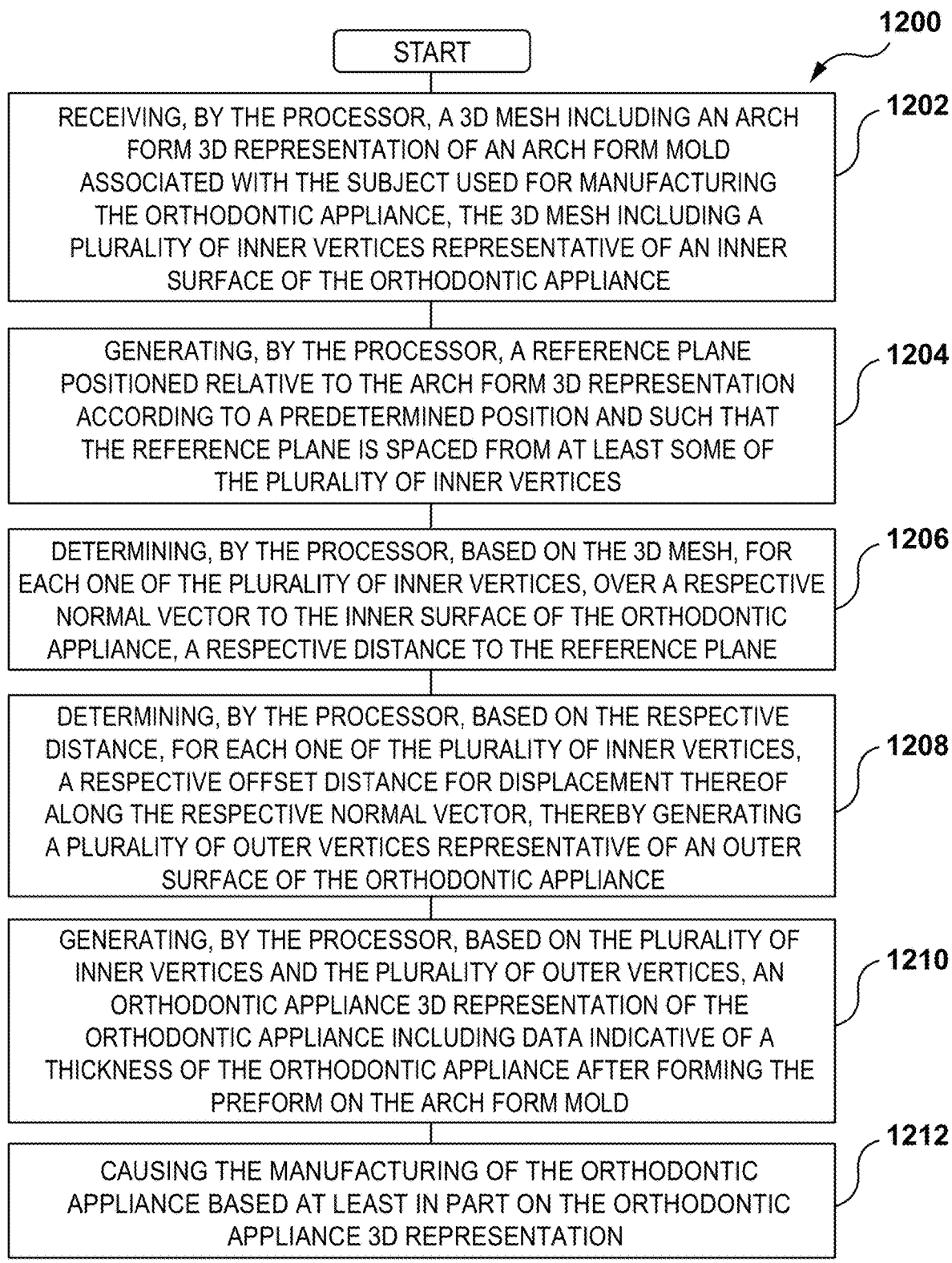
FIG. 12 depicts a flowchart of a method of manufacturing the orthodontic appliance of FIGS. 2A and 2B, according to certain embodiments of the present technology.

Given the architecture and the examples provided hereinabove, it is possible to execute a method for manufacturing an orthodontic appliance for the subject—such as the aligner 10. With reference now to FIG. 12, there is depicted a flowchart of a method 1200, according to certain non-limiting embodiments of the present technology. The method 1200 may be executed by the processor 550 of the system 400.

Step 1202: Receiving, by the Processor, a 3D Mesh Including an Arch Form 3D Representation of an Arch Form Mold Associated with the Subject Used for Manufacturing the Orthodontic Appliance, the 3D Mesh Including a Plurality of Inner Vertices Representative of an Inner Surface of the Orthodontic Appliance The method commences at step 1202 where the processor 550 may be configured to receive a 3D mesh the aligner mold associated with the subject, such as the single 3D mesh 650 depicted in FIG. 6, the single 3D mesh 650 including the aligner mold 3D representation 600 indicative of the inner surface 12 of the aligner 10 and the support surface 3D representation 610 indicative of the support surface, on which the aligner mold (not depicted) of the aligner 10 is to be positioned during the manufacturing the aligner 10. Thus, the single 3D mesh 650 comprises the plurality of inner vertices 660 indicative of an inner surface of the unfinished aligner 300.

In some non-limiting embodiments of the present technology, the processor 550 may be configured to generate the aligner mold 3D representation 600 based on the predetermined orthodontic treatment. In specific non-limiting embodiments of the present technology, the processor 550 may be configured to determine the orthodontic treatment based on the arch form 3D representation representative of the actual configuration of the lower arch form 20 as described in the co-owned U.S. Pat. No. 10,993,782-B1 issued on May 4, 2021, and entitled "SYSTEMS AND METHODS FOR DETERMINING A TOOTH TRAJECTORY"; the content of which is hereby incorporated by reference in its entirety.

In some non-limiting embodiments of the present technology, the processor 550 may be configured to generate the single 3D mesh 650 based on the aligner mold 3D representation 600 and the support surface 3D representation 610 received as separate meshes, and further combine them into the single 3D mesh 650.

The method 1200 thus proceeds to step 1204.

Step 1204: Generating, by the Processor, a Reference Plane Positioned Relative to the Arch Form 3D Representation According to a Predetermined Position and Such that the Reference Plane is Spaced From at Least Some of the Plurality of Inner Vertices At step 1204, according to certain non-limiting embodiments of the present technology, the processor 550 may be configured to generate the cover surface 750 encompassing the plurality of inner vertices 660 as depicted in FIG. 7.

To that end, first, the processor 550 may be configured to determine the reference plane 760. For example, according to some non-limiting embodiments of the present technology, the reference plane 760 may be generated to be inclined to the base portion 615 of the support surface 3D representation 610 at a predetermined angle—such as 3, 5, or 10 degrees, as an example. In other non-limiting embodiment of the present technology, the processor 550 may be configured to generate the reference plane 760 to extend through at least some of the plurality of inner vertices 660. In specific non-limiting embodiments of the present technology, the reference plane 760 may extend through outermost ones of the plurality of inner vertices 660 representative of the occlusal surfaces of respective ones of the lower teeth 16.

Further, based on the reference plane 760, the processor 550 may be configured to generate the cover surface 750 as described above with reference to FIG. 7.

In additional non-limiting embodiments of the present technology, the processor 550 may be configured to remove those of the plurality of inner vertices 660 representative of the generatrix portion 620 of the support surface 3D representation 610 of the single 3D mesh 650, thereby generating the unfinished aligner mold 3D representation 800 depicted in FIG. 8.

Further, the processor 550 may be configured to redistribute the plurality of inner vertices 660 along the surface of the unfinished aligner mold 3D representation 800 uniformly by remeshing the surface as described above with reference to FIGS. 9A and 9B.

The method 1200 thus advances to step 1206.

Step 1206: Determining, by the Processor, Based on the 3D Mesh, for Each One of the Plurality of Inner Vertices, Over a Respective Normal Vector to the Inner Surface of the Orthodontic Appliance, a Respective Distance to the Reference Plane At step 1206, according to certain non-limiting embodiments of the present technology, the processor 550 may be configured to determine the respective distances from each one of the plurality of inner vertices 660 to the cover surface 750. To that end, as described above with reference to FIG. 10A, the processor 550 may be configured to: (1) determine the plurality of normal vectors 1060; and (2) determine each one of the respective distances along a respective one of the plurality of normal vectors 1060—such as the given distance p from the respective inner vertex 1064 to the cover surface 750 along the given normal vector 1062, as an example.

According to certain non-limiting embodiments of the present technologies, the respective distances thus determined are indicative of the aligner thickness distribution of the aligner 10, which the processor 550 can be configured to determine based on the respective distances.

In additional non-limiting embodiments of the present technology, the processor 550 may be configured to visualize the respective distances on the unfinished aligner mold 3D representation 800. For example, as described above with reference to FIG. 10B, the processor 550 may be configured to generate, based on the respective distances, the heat map representation 1070. Further, the processor 550 may be configured to store the heat map representation 1070 in one of the solid-state drive 560 and the random access memory 570 for further causing displace thereof in the screen 422.

The method 1200 hence advances to step 1208.

Step 1208: Determining, by the Processor, Based on the Respective Distance, for Each One of the Plurality of Inner Vertices, a Respective Offset Distance for Displacement Thereof Along the Respective Normal Vector, Thereby Generating a Plurality of Outer Vertices Representative of an Outer Surface of the Orthodontic Appliance At step 1208, according to certain non-limiting embodiments of the present technology, the processor 550 may be configured to determine the aligner thickness distribution based on the respective distances from each one of the plurality of inner vertices 660 to the cover surface 750.

To that end, as mentioned above, the processor 550 may be configured to determine the respective thickness values associated with each one of the plurality of inner vertices 660. For example, based on the given distance p, the processor 550 may be configured to determine a respective thickness value of the aligner 10 associated with the respective inner vertex 1064 according to Equations (1) and (2).

By so doing, according to certain non-limiting embodiments of the present technology, the processor 550 may be configured to determine the respective thickness values of the aligner thickness distribution of the aligner 10 at each one of the plurality of inner vertices 660.

Further, as described above with reference to FIG. 11A, based on the respective thickness values, the processor 550 may be configured to determine the plurality of outer vertices 1160. For example, the processor 550 may be configured to determine the given outer vertex 1164 of the plurality of outer vertices 1160 by offsetting the respective inner vertex 1064 at the given thickness value $\|n\|$, determined therein in accordance with Equation (1), along the given normal vector 1062 of the plurality of normal vectors 1060. Thus, the processor 550 may be configured to determine the plurality of outer vertices 1160 defining the unfinished aligner outer surface 1180 of the unfinished aligner 300.

The method 1200 thus proceeds to step 1210.

Step 1210: Generating, by the Processor, Based on the Plurality of Inner Vertices and the Plurality of Outer Vertices, an Orthodontic Appliance 3D Representation of the Orthodontic Appliance Including Data Indicative of a Thickness of the Orthodontic Appliance After Forming the Preform on the Arch Form Mold At step 1210, according to certain non-limiting embodiments of the present technology, the processor 550 may be configured to generate, based on the plurality of inner vertices 660 and the plurality of outer vertices 1160, the unfinished aligner 3D representation 1300 of the unfinished aligner 300, depicted in FIG. 11B. The unfinished aligner 3D representation 1300 can thus be indicative of the aligner thickness distribution of the aligner 10.

The method 1200 thus advances to step 1212.

Step 1212: Causing the Manufacturing of the Orthodontic Appliance Based at Least in Part on the Orthodontic Appliance 3D Representation Finally, at step 1212, according to certain non-limiting embodiments of the present technology, based on the unfinished aligner 3D representation 1300, the processor 550 may be configured to cause manufacturing the aligner 10.

To that end, as described above, the processor 550 may be configured to: (1) obtain data indicative of the position of the cut line 304 within the unfinished aligner 300; (2) apply the data to the unfinished aligner 3D representation 1300; (3) based on the unfinished aligner 3D representation 1300, determine the cut line thickness of the aligner 10 along the cut line 304; and (4) based on the cut line thickness, determine the parameters of the forming subsystem 450 for cutting, by the cutting device 454, the unfinished aligner 300 along the cut line 304, thereby forming the aligner 10.

In some non-limiting embodiments of the present technology, the parameters of the forming subsystem 450 determined by the processor 550 for cutting may comprise parameters of the cutting device 454 associated with intensity of cutting, such as power, as an example. In some non-limiting embodiments of the present technology, the parameters associated with the intensity of cutting may include the speed of cutting and the distance between the cutting device 454 and the unfinished aligner 300.

Further, according to certain non-limiting embodiments of the present technology, the processor 550 may be configured to modulate the parameters of the cutting device 454 based on the trade-off between the consumed power of the cutting device 454 and the predetermined level of smoothness of thus to be produced open edge of the channel 26 of the aligner 10, thereby providing more optimized power consumption of the cutting device 454.

For example, causing higher intensity of the cutting—for example, by at least one of increasing the speed of cutting and decreasing the distance between the cutting device 454 and the unfinished aligner 300—through portions of the unfinished aligner 300 having greater values of the cut line thickness, the processor 550 may be configured to reduce such cutting defects of the open edge of the channel 26 as striations or buffings, as an example. In another example, causing lower intensity of the cutting—for example, by at least one of decreasing the speed of cutting and increasing the distance between the cutting device 454 and the unfinished aligner 300—through portions of the unfinished aligner 300 having smaller values of the cut line thickness, the processor 550 may be configured to reduce such cutting defects as overburns (in the embodiments, where the cutting device 454 is one the laser cutting device and the mechanical cutting device) resulting in a charred open edge of the channel 26 of the aligner 10.

Further, in some non-limiting embodiments of the present technology, based on the so determined parameters of the cutting device 454, the processor 550 may be configured to cause the forming subsystem 450 to cut the unfinished aligner 300 along the cut line 304 as described above.

In yet other non-limiting embodiments of the present technology, the processor 550 may be configured to model, based on the data indicative of the position of the cut line 304, the aligner 3D representation (not depicted) of the aligner 10 from the unfinished aligner 3D representation 1300; cause manufacturing the aligner 10 based on the aligner 3D representation (not depicted) using 3D printing techniques.

Thus, certain embodiments of the method 1200 allow cutting the unfinished aligner 300 of higher quality, thereby producing a smoother open edge of the channel 26 of the aligner 10 while optimizing power consumption of the cutting device 454.

The method 1200 thus terminates.

Modifications and improvements to the above-described implementations of the present technology may become apparent to those skilled in the art. The foregoing description is intended to be exemplary rather than limiting. The scope of the present technology is therefore intended to be limited solely by the scope of the appended claims.

The invention claimed is:

1. A method of manufacturing an orthodontic appliance for a subject, the method being executable by a processor, the method comprising:

receiving, by the processor, a 3D mesh including an arch form 3D representation of an arch form mold associated with the subject used for manufacturing the orthodontic appliance, the arch form mold being representative of subject's teeth to which the orthodontic appliance is to be applied, the 3D mesh including a plurality of inner vertices representative of an inner surface of the orthodontic appliance;

generating, by the processor, a cover surface encompassing the plurality of inner vertices of the 3D mesh, such that the cover surface is spaced from at least some of the plurality of inner vertices;

determining, by the processor, based on the 3D mesh, for each one of the plurality of inner vertices, a respective distance therefrom to the cover surface, the respective distance associated with a given inner vertex being indicative of a thickness of the orthodontic appliance after forming a preform on the arch form mold;

determining, by the processor, based on the respective distance, for each one of the plurality of inner vertices, a respective offset distance for displacement thereof along the respective normal vector, thereby generating a plurality of outer vertices representative of an outer surface of the orthodontic appliance;

generating, by the processor, based on the plurality of inner vertices and the plurality of outer vertices, an orthodontic appliance 3D representation of the orthodontic appliance including data indicative of the thickness of the orthodontic appliance after forming the preform on the arch form mold;

causing the manufacturing of the orthodontic appliance based at least in part on the orthodontic appliance 3D representation.

2. The method of claim 1, wherein the 3D mesh further includes, along with the arch form 3D representation:
a support surface 3D representation indicative of a support surface used for forming the orthodontic appliance from the preform, the arch form 3D representation being positioned on the support surface 3D representation.

3. The method of claim 2, wherein the generating the cover surface includes generating a reference plane extending through at least some of those of the plurality of inner vertices corresponding to occlusal surfaces of respective ones of the subject's teeth, such that:
the cover surface includes the reference plane and at least a portion of the support surface 3D representation.

4. The method of claim 1, further comprising converting the 3D mesh into a voxel space and obtaining the plurality of inner vertices therefrom,
the plurality of inner vertices having been redistributed within the 3D mesh uniformly.

5. The method of claim 1, further comprising obtaining data indicative of a cut line for the orthodontic appliance, and wherein the manufacturing comprising causing, by the processor, cutting, by a cutting device, the orthodontic appliance along the cut line.

6. The method of claim 5, wherein the cutting device includes a laser apparatus, and wherein the causing comprises modulating, by the processor, a parameter of the laser apparatus based on the thickness of the orthodontic appliance 3D representation along the cut line.

7. The method of claim 1, further comprising determining, by the processor, the cut line for the orthodontic appliance based at least on the 3D mesh.

8. The method of claim 7, further comprising determining, based on the orthodontic appliance 3D representation, a thickness of the orthodontic appliance along the cut line; and the manufacturing comprising, based on the thickness of the orthodontic appliance along the cut line, causing, by the processor, a cutting device to cut the orthodontic appliance along the cut line.

9. The method of claim 1, further comprising:
visualizing, on the orthodontic appliance 3D representation, the respective distances associated with the inner plurality of vertices, thereby generating a heat map representative of a thickness distribution within the orthodontic appliance;

storing the orthodontic appliance 3D representation including the heat map; and causing display of the orthodontic appliance 3D representation including the heat map on a display.

10. The method of claim 1, wherein a given offset distance associated with a respective one of the plurality of inner vertices is determined based on the following equation:

$$\|n\|=h-kp,$$

where n is the given offset distance;
h is an initial thickness of the preform;
k is a predetermined coefficient; and
p is a respective distance from the respective one of the plurality of inner vertices to the cover surface having been determined along the respective normal vector.

11. The method of claim 10, wherein the predetermined coefficient is determined such that the following equation is satisfied:

$$V_o = V_f$$

where $V_o$ is a volume of the preform; and
$V_f$ is a volume of the orthodontic appliance.

12. A system for manufacturing an orthodontic appliance, the system comprising:
a processor;
a non-transitory computer-readable medium comprising instructions;
the processor, upon executing the instructions, being configured to:
receive a 3D mesh including at least an arch form 3D representation of an arch form mold associated with the subject used for manufacturing the orthodontic appliance, the arch form mold being representative of subject's teeth to which the orthodontic appliance is to be applied, the 3D mesh including a plurality of inner vertices representative of an inner surface of the orthodontic appliance, the 3D mesh;
generate a cover surface encompassing the plurality of inner vertices of the 3D mesh, such that the cover surface is spaced from at least some of the plurality of inner vertices;
determine, based on the 3D mesh, for each one of the plurality of inner vertices, over a respective normal vector to the inner surface of the orthodontic appliance, a respective distance to the reference plane,
the respective distance associated with a given inner vertex being indicative of a thickness of the orthodontic appliance after forming a preform on the arch form mold;
determine, based on the respective distance, for each one of the plurality of inner vertices, a respective offset distance for displacement thereof along the respective normal vector, thereby generating a plurality of outer vertices representative of an outer surface of the orthodontic appliance;
generate, based on the plurality of inner vertices and the plurality of outer vertices, an orthodontic appliance 3D representation of the orthodontic appliance including data indicative of the thickness of the orthodontic appliance after forming the preform on the arch form mold;

cause manufacturing of the orthodontic appliance based at least in part on the orthodontic appliance 3D representation.

13. The system of claim 12, wherein the 3D mesh further includes, along with the arch form 3D representation:
a support surface 3D representation indicative of a support surface used for forming the orthodontic appliance from the preform, the arch form 3D representation being positioned on the support surface 3D representation.

14. The system of claim 13, wherein to generate the cover surface, the processor is configured to generate a reference plane extending through at least some of those of the plurality of inner vertices corresponding to occlusal surfaces of respective ones of the subject's teeth, such that:
the cover surface includes the reference plane and at least a portion of the support surface 3D representation.

15. The system of claim 12, wherein the processor is further configured to convert the 3D mesh into a voxel space and obtaining the plurality of inner vertices therefrom,
the plurality of inner vertices having been redistributed within the 3D mesh uniformly.

16. The system of claim 12, further comprising a cutting device communicatively coupled with the processor, and wherein the processor is further configured to:
obtain data indicative of a cut line for the orthodontic appliance;
cause the cutting device to cut the orthodontic appliance along the cut line.

17. The system of claim 12, wherein the processor is configured to determine the cut line for the orthodontic appliance based at least on the 3D mesh.

18. The system of claim 17, wherein the processor is further configured to determine, based on the orthodontic appliance 3D representation, a thickness of the orthodontic appliance along the cut line; and the manufacturing comprising, based on the thickness of the orthodontic appliance along the cut line, causing, by the processor, a cutting device to cut the orthodontic appliance along the cut line.

19. The system of claim 12, wherein the processor is further configured to:
visualize, on the orthodontic appliance 3D representation, the respective distances associated with the inner plurality of vertices, thereby generating a heat map representative of a thickness distribution within the orthodontic appliance;
store the orthodontic appliance 3D representation including the heat map; and
cause display of the orthodontic appliance 3D representation including the heat map on a display.

20. The system of claim 12, wherein the processor is configured to determine a given offset distance associated with a respective one of the plurality of inner vertices based on the following equation:

$$\|n\| = h - kp,$$

where n is the given offset distance;
h is an initial thickness of the preform;
k is a predetermined coefficient determined such that the following equation is satisfied:

$$V_0 = V_f,$$

where $V_0$ is a volume of the preform;
$V_f$ is a volume of the orthodontic appliance; and
p is a respective distance from the respective one of the plurality of inner vertices to the cover surface having been determined along the respective normal vector.

* * * * *